United States Patent [19]

Colvin

[11] Patent Number: 5,422,276

[45] Date of Patent: Jun. 6, 1995

[54] STERILIZER TEST METHOD AND APPARATUS

[76] Inventor: Richard R. Colvin, Orchard Hill Rd., Katonah, N.Y. 10536

[21] Appl. No.: 263,792

[22] Filed: Jun. 22, 1994

Related U.S. Application Data

[63] Continuation-in-part of Ser. No. 878,564, May 5, 1992, abandoned.

[51] Int. Cl.6 .......................... G01N 30/54; A61L 2/24
[52] U.S. Cl. ............................................. 436/1; 436/3; 422/109; 422/26; 422/116
[58] Field of Search ........................................ 436/1–3, 436/6–7; 422/26, 298, 109–111, 116

[56] References Cited

U.S. PATENT DOCUMENTS

| | | | |
|---|---|---|---|
| 3,967,494 | 7/1976 | Joslyn | 73/29 |
| 3,982,893 | 9/1976 | Joslyn | 21/2 |
| 4,115,068 | 9/1978 | Joslyn | 422/56 |
| 4,372,916 | 2/1983 | Chamberlain et al. | 422/111 |
| 4,486,387 | 12/1984 | Augurt | 422/58 |
| 4,594,223 | 6/1986 | Dyke et al. | 422/56 |
| 4,596,696 | 6/1986 | Scoville | 422/61 |
| 4,909,070 | 3/1990 | Smith | 324/690 |
| 5,066,464 | 11/1991 | Augurt | 422/58 |

OTHER PUBLICATIONS

Good Hospital Practice: Steam Sterilization and Sterility Assurance, AAMI, Arlington, Va. 1980.
Bowie, J. H. et al, The Bowie and Dick Autoclave Tape Test, The Lancet, Mar. 16, 1963, pp. 586–587.
Joslyn cited Darmody, et al (1964), Disinfection, Sterilization and Preservation, S. Block, ed., 3rd Edition, 1983, p. 23.
Joslyn, L. H., Sterilization by Heat, Disinfection, Sterilization and Preservation, S. Block, ed., 3rd Edition, 1983, p. 17.
Bowie, J. H., Dr. John Bowie on the Bowie and Dick Test, Journal HSPD, Mar./Apr. 1984, pp. 26–28.
Mayworm, D., The Bowie–Dick type test . . . Are there alternative ways? Journal HSPD, Mar./Apr. 1984,, pp. 31–34.
Ryan, P., The Bowie–Dick type test . . . The discrepancies between theory and practice, Journal HSPD, Mar.-/Apr. 1984, pp. 20–24.

Primary Examiner—Lyle A. Alexander
Attorney, Agent, or Firm—St. Onge Steward Johnston & Reens

[57] ABSTRACT

A method and apparatus assures effective operation of sterilizers, especially those of the pre-vacuum type. The apparatus performs two principal methods: (1) testing for completeness of air removal from a sterilizer chamber, including the re-entrainment of air in the load due to air leaks in the chamber, vacuum system and/or steam system, and (2) the testing for effective sterilization conditions. Also, performed are three secondary methods: (i) identifying of causes of sterilizer faults, (ii) providing of preventive maintenance procedures (an Early Warning) (iii) identifying of procedures to correct sterilization faults in progress. These methods are illustrated for the two principal modes of operation: (a) the performance of a Bowie and Dick type test, as is usually done on a once-a-day basis; and (b) monitoring the sterilizer during load conditions.

19 Claims, 14 Drawing Sheets $$Y = F\left(\sum_{1=0}^{n} W_1 X_1\right)$$

WHERE $F(I) = \dfrac{1}{1+e^{-1}}$ (SIGMOID)

STERILIZER TEST METHOD AND APPARATUS

RELATED APPLICATION

The present application is a Continuation-in-part of application Ser. No. 07/878,564, filed May 5, 1992, now abandoned in the names of Richard R. Colvin and Herbert Perten.

TECHNICAL FIELD

The invention relates to sterilizers and, in particular, to a method and apparatus for improving the assurance of effective operation of sterilizers, especially those of the pre-vacuum type.

Reusable medical and surgical supplies must be cleaned and sterilized before storage for reuse. While absolute sterility may not be possible and testing for it is virtually impossible, strict adherence to stringent procedures can provide confidence that no viable organisms should survive. Items like dressings, gowns, drapes, and instruments must be stored ready for use, and it is essential that procedures assure that no unprocessed packages are designated sterile.

Steam sterilization is the preferred method for use on an ongoing basis in hospitals. Conventional hospital practice entails the use of heat-activated indicator tape on each package to identify packages which have been treated in the sterilizer. The tape changes color when heated sufficiently by the steam. A changed color does not, however, assure that the contents of the package have been heated sufficiently. This is assured only by rigorous adherence to established procedures for operating the sterilizer and for assuring its effectiveness when operated properly.

These procedures have been developed by the Association for Advancement of Medical Instrumentation (AAMI) and are described in *Good Hospital Practice: Steam Sterilization and Sterility Assurance* published by the AAMI, 3330 Washington Boulevard, Arlington, Va. 22209.

Another procedure recommended by AAMI is the use of biological indicators (BI's) to document the efficacy of specific steam sterilization cycles. Biological indicators, consisting of spores of *Bacillus stearothermophilus*, known to be most resistant to steam sterilization, enable the user to ascertain whether products have been subject to sterilization conditions after the indicator has been incubated for 24 hours to check for growth. BI's have the ability to integrate time, temperature, steam quality and other conditions without physically influencing environmental conditions in order to document that the conditions were correct for an effective sterilization process.

The AAMI recommends biological-indicator test packs should be used routinely in sterilization loads at least weekly, but preferably daily. Each load containing an implantable device must be monitored and, whenever possible, the implantable device quarantined until results of the biological testing are available.

Air within packs, and to a lesser extent the quality of steam in terms of superheating or wetness, can prevent a steam sterilizer from achieving its objective even though the proper times and temperatures are indicated on the sterilizer instruments. Short cycle times are preferred, but can be effective only when saturated steam directly contacts the objects of sterilization to permit transfer of the latent heat of vaporization to the objects and any microbiological contamination. Superheated steam does not condense as much steam as fully saturated steam and thus gives up less latent heat. In this regard, superheated steam is similar to hot air which alone can sterilize, but takes much longer and has the further problem that it does not mix well or penetrate as well as steam. As a practical matter, air is an insulator. Wet steam can hinder diffusion of air from packages to be sterilized.

An additional problem occurs when packages that are being sterilized become excessively wet so they can not be dried during the sterilizer's preprogrammed drying cycle. The packages leave the sterilizer still wet and the wetness is a vector for recontamination. Good hospital practice in Central Supply requires that these packages be opened, the linens again be laundered, re-packaged and then put through another sterilization cycle.

At the present time there is no means for detecting a wet pack condition, and correcting this condition causes additional work and expense.

The presence of air in a steam sterilizer has always been a problem to be avoided. The combined effect of pressure in the sterilizer and the condensation of steam in the packages tends to concentrate the air deep within the packages —preventing direct steam contact with the objects. To better free the sterilizer of air, many modern steam sterilizers employ a preliminary air evacuation step. It is essential that evacuation be effective and that air not leak into the chamber, vacuum or steam systems so that air does not have a chance to inhibit sterilization. Unfortunately, leaks of air are not uncommon. One investigator (Joslyn, citing Darmody, eta/. (1964)in Disinfection, Sterilization and Preservation; S. Block, Ed.; Third Edition, 1983, page 23) reported that not one of ten pre-vacuum sterilizers tested was able to meet and maintain recommended conditions.

In 1963, a test was suggested by researchers J. H. Bowie and J. Dick to determine if a pre-vacuum sterilizer was operating effectively in detecting defects in the sterilization equipment, namely the inadequacy of the initial vacuum so air remains in the packages to be sterilized and air leaks within the chamber, vacuum and or steam systems so air becomes re-entrained in the packages. (See J. H. Bowie, J. C. Kelsey, G. R. Thompson; The Bowie and Dick Autoclave Tape Test; *The Lancet*, Mar. 16, 1963, pp 586-7; see also L. Joslyn, "Sterilization by Heat," *Disinfection, Sterilization and Preservation*; S. Block, Ed.; Third Edition, 1983, page 17)

The Bowie and Dick procedure involved preparing a test package containing at least about 25 huckaback towels folded into eight thicknesses and stacked to a height of 10–11 inches, a sheet of unglazed paper bearing a cross of a specific heat-sensitive tape placed in the middle of the stack, and a suitable wrapping. The towels serve as a heat sink, condensing the steam—utilizing the latent heat for sterilization. Any air present remains uncondensed. The test utilizes the phenomenon that steam condenses and air does not. A nonuniform color change on the tape after subjecting the package to a complete sterilization cycle, indicated that air was present and sterility could not be assured. A uniform color change supported by a record showing a satisfactory time—temperature relationship (in the chamber drain) indicated a satisfactory result and could be interpreted as showing rapid steam penetration, adequate air removal, and freedom from significant air leaks.

The Bowie and Dick test was, however, subject to wide variations in the manner in which it was performed, and its results were very subjective. Indeed, one survey revealed that no two central service departments from a total of 35 interviewed, performed the Bowie and Dick test in the same way. (P. Ryan, "The Bowie-Dick type test . . . The discrepancies between theory and practice," *Journal HSPD*, March/April 1984, pp. 20–24.) Another survey indicated the accuracy of interpreting test scores was only 60–80% at the beginning of a study. (D. Mayworm, "The Bowie-Dick type test . . . Are there alternative ways?" *Journal of Hospital Supply, Processing and Distribution (Journal HSPD)*, March/April 1984, pp. 31–34.) The reliability of steam sterilizers in the medical field remains an active area of concern and research.

For over 30-years the Bowie & Dick test has been the accepted test for determining if a pre-vacuum sterilizer is operating correctly in terms of evacuating air from the chamber and not leaking air into the chamber, steam or vacuum lines after the evacuation step. In addition to the limitations of the test cited above, the co-inventor of the Bowie and Dick test, Dr. John Bowie discussed the test he invented in an interview published in the *Journal HSPD*, March/April 1984, pp.26–28. He concluded the interview by saying:

I am now thinking that new test equipment should be developed which would be incorporated into the automatic control of the sterilizer and looked after as part of the normal servicing procedure of the steriliser. Those responsible for operating the steriliser would merely have to note whether the final signal given by the automatic control said "sterilization assured if packing correct" or "sterilisation not assured."

Bowie and Dick type tests are typically run once a day and, if the challenges (air trapped deep within dense porous packs and air leaks that entrain air within lightly packed porous packs) are not too severe and the tests are run and interpreted correctly, can determine only the condition of air leakage and can determine it only at that time. The sterilizer operations, which are actually responsible for assuring the safety of patients, are conducted under load conditions and cannot be monitored with accuracy with current technology because of what is known as the small-load effect whereby air in the chamber will concentrate in a small load for maximum detection, but when other packs are in the chamber will be divided among them. There is a present need for a more objective, less subjective, more accurate test for adequate air removal from a test cycle.

There is also a present need for a test which can reliably, automatically monitor sterilization conditions, in loaded cycles where goods are being processed for use in patient care. Currently, the only way to monitor sterilization conditions in a loaded cycle is with a biological indicator. But these indicators require up to 24-hours of incubation before they will reveal if conditions for sterilization have been meet. At one point, the Association of Operating Room Nurses (AORN), recommended in Standards and Recommended Practices for Sterilization, that a Bowie and Dick test be conducted for every cycle in a prevacuum sterilizer. The AORN later withdrew this recommendation. The small-load phenomenon will invalidate a Bowie and Dick test in a loaded cycle.

BACKGROUND ART

Over the years, a number of devices and techniques have been proposed to provide a greater degree of assurance that a sterilizer is operating effectively to exclude air which could prevent direct contact of steam with the objects being sterilized. In some cases, these have been adopted by hospitals convinced that they needed more reliability.

Efforts to mechanically assure the complete removal of air from steam sterilizers have not been fully successful. Prior to the publication of the Bowie and Dick test in 1963, co-developer J. Dick had employed thermocouples in a simpler form of the test, one in a test package and another at the sterilizer drain. With most loads like the towel package, however, it is not possible to predict the location of the air bubble with the certainty required. The published version of the test replaced the thermocouple with a heat-sensitive tape laid down in two strips in the shape of a St. Andrew's cross to better indicate the extent of air incorporation, but still required monitoring drain temperatures.

In U.S. Pat. No. 3,982,893, Joslyn provides an electronic device that is used with loads of uncontrolled size and character, contrary to the Bowie and Dick protocol which requires the test to be performed on an empty chamber. The Joslyn ('893) device does not provide a controlled challenge to the passage of steam to assure condensation of a sufficient amount to leave behind a detectable amount of air and provides no means for determining if an air bubble exists or might be located. In packs, of the type shown by Joslyn ('893) it is simply not possible to predict where an air bubble might reside. This can be a fatal error.

In U.S. Pat. No. 3,967,494, Joslyn disclosed a method and apparatus for detecting entrapped air in a steam sterilizer. The device is shown outside the steam chamber to enable quantitative measurement of the amount of air or other non-condensable gas at the chamber drain. The device is intended for use with a sterilizer of the type that employs steam to displace air. The device does not, however, eliminate the need for a Bowie and Dick test.

In U.S. Pat. No. 4,309,381 and 4,372,916, Chamberlain and Cook monitor the temperature of the exhausted steam at the drain and the pressure within the chamber, and compare these to the steam table values to determine if all the air has been evacuated by concluding somehow that if fully saturated steam is present no air can be in the chamber. Chamberlain fails to recognize that air in an enclosed chamber with steam will have the same pressure as steam and the same temperature as steam (though not the latent heat energy of steam) and that water droplets can be entrained in fully saturated steam. Thus, this patent cannot achieve the results of the present invention which provides the objective results which Dr. Bowie stated were needed but not available.

In U.S. Pat. No. 4,115,068, Joslyn describes a small device for indicating air inside a sterilization chamber of the type used with steam or ethylene oxide. The device includes an upright tube holding a thermo-sensitive indicator strip and a heat sink. Air is said to pass into the tube where it interferes with the steam contacting the thermo-sensitive indicator strip.

Dyke and Oshlag comment on this arrangement in U.S. Pat. No. 4,594,223, indicating that steam, which is less dense than air, is required to work against gravity, the weight of any accumulated air and the downward moving condensate. They also comment that the condensate forms in the same chamber in which the indicator strip is located and can contact the strip so heat from incoming steam can vaporize the condensate on the strip, thereby interfering with the results. To correct this, they describe a device having a depending glass chamber which permits air to settle to the bottom along with water from condensed steam.

The Dyke and Oshlag device, like that of Joslyn, is simply a replacement for the Bowie and Dick test and requires interpretation of the test results—a source of frequent errors in the original Bowie and Dick test. This is true also of a related device disclosed by Augurt in U.S. Pat. No. 5,066,464, which has a strip of heat-sensitive material in a horizontally-disposed chamber. Similarly, U.S. Pat. No. 4,486,387 to Augurt and U.S. Pat. No. 4,596,696 to Scoville, describe disposable test packages which have Bowie and Dick type test sheets which require interpretation.

In U.S. Pat. Nos. 4,486,387 and 5,066,464, both to Augurt, a requirement is described to provide a challenge for the two most common flaws: 1) an inadequate initial vacuum that leaves air within the packs; 2) air leaks in the chamber, vacuum and/or steam system that permits reentrainment of air in the packs. Those inventions offer a compromise.

There remains a need for a method and apparatus to more objectively, reliably, and precisely determine if a sterilizer is working correctly and to monitor its operation. There is especially a need for a test which provides a positive indication of problems or the absence of them and decreases the probability that either (1) the test performance or (2) interpretation of the results will be dependent upon the skills of a particular operator— both, areas of concern in Bowie and Dick testing.

DISCLOSURE OF INVENTION

It is an object of the invention to provide a test method and apparatus to determine the effective air removal from a steam sterilizer and the presence of air leaks within the chamber, vacuum or steam systems after the air evacuation cycle has been completed with less subjectivity, and therefore, greater accuracy than the Bowie and Dick test and thereby reduce common causes of error in Bowie and Dick type tests.

It is another and more specific object of the invention to provide a method and apparatus for monitoring a steam sterilizer operation under load conditions for the presence of wet steam, superheated steam and air.

It is another object of the invention to provide a method and apparatus for monitoring the sterilization conditions within a steam sterilizer for operation under load conditions that will compensate for the division of any air in the chamber among the packs so that critical amounts of air in the chamber can be detected.

It is yet another object of the invention to provide an apparatus and method for determining the effective air removal from the chamber of a steam sterilizer and the presence of air leaks within the chamber, vacuum or steam systems and/or steam quality therein by placing a portable test unit in the chamber and either recording locally the data sensed by the unit or transmitting it by radio, infrared or ultrasonic means to a receiver outside the chamber.

It is an object of the invention to provide a method and apparatus for monitoring a steam or ethylene oxide (EO) sterilizer operation by placing a portable test unit in the chamber and either recording locally the data sensed by the unit or transmitting it by radio, infrared or ultrasonic means to a receiver outside the chamber to determine causes for air in the chamber, superheat, and wetpacks and other conditions detrimental to sterilization.

It is a further object of the invention to provide a method and apparatus for identifying action to remedy a wet pack condition when data is being transmitted by radio, infra red or ultrasonic means to a receiver and controller outside the sterilizer.

It is a further object of the invention to provide an early warning system for a steam sterilizer which can determine the effective air removal from a pre-vacuum sterilizer and the presence of air leaks within the chamber, vacuum or steam systems by comparing current readings to either or both of standard values and average values for recent test runs for both a Bowie and Dick test cycle mode and for operation under load conditions.

These and other objects are accomplished by the present invention which provides methods and apparatus for determining the effectiveness of air removal from a steam sterilizer, for the detection of air leaks and for monitoring the sterilization conditions therein, by dynamically channeling air to sensors and monitoring the time-temperature history at the sensors. The apparatus provides a test device, a controller and a system comprised of both. The methods achieve the objects of the invention in its broad as well as specific aspects.

In one of its preferred forms, a test device comprises: a test module including wall members defining at least two (n) test cavities having openings at one end of each to permit entrance of ambient gases, temperature sensors, or other sensing means such as oxygen sensors, capable of generating signals ($T_1, T_2 \ldots T_n$) indicative of the temperatures at their locations at the ends of the test cavities opposite from said openings, and heat sinks located in said test cavities between said openings and the ends of the said test cavities.

In the preferred form, the test device further comprises a data acquisition and transmission unit which has the capability of recording the signals and signals representative of the time at which they were taken, preferably stored for transmission.

In another of its preferred forms the device will comprise a data acquisition and transmission unit which has the capability of recording signals representative of temperatures sensed at defined locations within a sterilization chamber and recording those signals and signals representative of the times at which they were taken, comprising means for converting analog temperature signals to digital forms; means for assigning a time for each temperature signal and means for transmitting the signals to a remote location.

The controller in one of its preferred forms comprises: means for receiving signals ($T_1, T_2 \ldots T_n$) indicative of the temperatures at a number (n) of predetermined locations within the chamber of a steam sterilizer; means for generating a signal ($T_r$) indicative of a reference temperature, which can be either a preselected reference temperature such as the desired sterilization temperature or a calculated temperature such as the average of selected temperatures reported in the latest of a predetermined number of cycles of operation in either of two modes (namely, (1) Bowie and Dick test or (2) operation under load); means for comparing signals ($T_1, T_2 \ldots T_n$) to signal $T_r$; and means for generating a signal indicative of either a pass or fail condition based on the results of the comparison. The means for receiving the signals ($T_1, T_2 \ldots T_n$) can comprise a radio receiver or connector means to electrically couple the controller to the test device.

The system in one of its embodiments comprises: a test device including means for sensing temperatures at their locations and generating signals ($T_1, T_2 \ldots T_n$) indicative thereof, means for generating a signal ($T_r$) indicative of a reference temperature, as above; and a controller including means for comparing signals ($T_1, T_2 \ldots T_n$) to signal $T_r$, and means for generating a signal indicative of either a pass or fail condition based on the results of the comparison.

The method of the invention in one of its forms comprises: placing a test device capable of sensing at least two (n) temperatures within the chamber of a sterilizer, indicative of two of the most frequent faults, the inadequacy of the initial vacuum and air leaks in the chamber, vacuum system and/or steam system and generating signals ($T_1, T_2 \ldots T_n$) indicative of the sensed temperatures; generating signals ($T_1, T_2 \ldots T_n$); generating a signal $T_r$ indicative of a reference temperature; comparing signals ($T_1, T_2 \ldots T_n$) to signal $T_r$; and generating a signal indicative of either a pass or fail condition based on the results of the comparison.

BRIEF DESCRIPTION OF THE DRAWINGS

The invention will be better understood and its advantages will be more fully appreciated from the following description, especially when read in light of the accompanying drawings, wherein.

DESCRIPTION OF PREFERRED EMBODIMENTS

Figure 1:
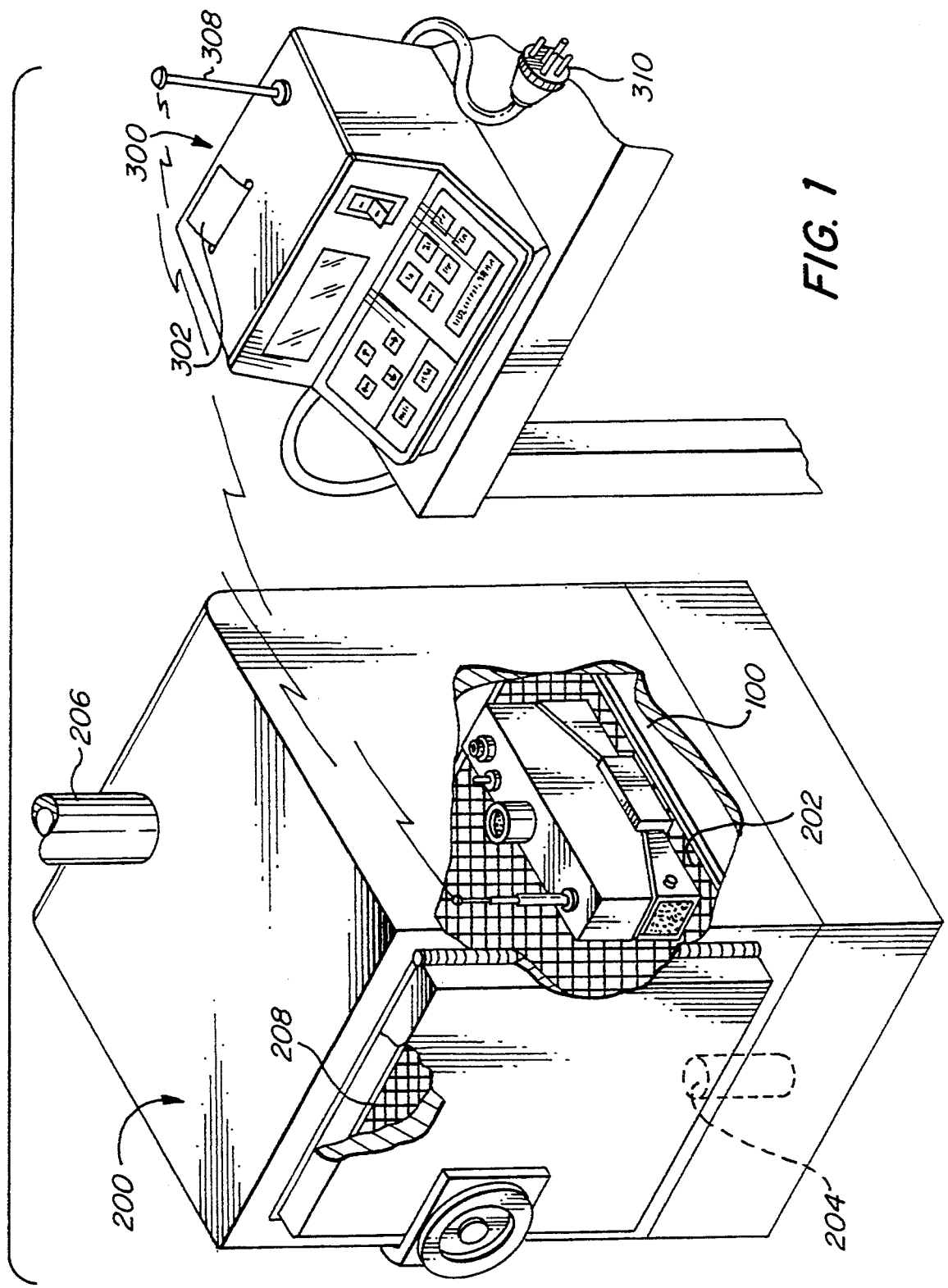
FIG. 1 is a perspective view of a preferred system of the invention including a test device inside the chamber of a steam sterilizer, positioned for recording test data and transmitting by radio to an external controller unit.

The description which follows will focus on a preferred test device and a preferred controller which together comprise a preferred system of the invention. This apparatus will be described in terms of the performance of the two principal method features of the invention: (1) the testing for completeness of air removal from a sterilizer chamber, including the re-entrainment of air in the load due to air leaks in the chamber, vacuum system and/or steam system, and (2) the testing for effective sterilization conditions. It will also be described in terms of the three secondary method features of the invention (i) the identifying of causes of sterilizer faults, (ii) the providing of preventive maintenance procedures (an Early Warning) (iii) the identifying of procedures to correct sterilization faults in progress. These methods will be illustrated for the two principal modes of operation: (a) the performance of a Bowie and Dick type test, as is usually done on a once-a-day basis; and (b) monitoring the sterilizer during load conditions. The invention will be described in the specific context of pre-vacuum steam sterilizers, but is not strictly limited to sterilizers of this type.

The invention operates on a different principal from the prior art—both the paper based tests and the electronic systems. The principal of operation of the chemical indicator paper-based systems is that because air does not condense and release latent heat like steam, air will not change the color of a heat-sensitive ink on a paper test panel in the time set for the steam to achieve the result. This is true even if the steam and the air are the same temperature. Chemical indicator, paper-based tests do not depend on the temperature differential between the air and the steam. They work on the principle of moist heat.

These tests—Bowie and Dick—are run in the absence of a load to test the operation of the sterilizer by checking for the presence of air. The air, if present under load conditions, could concentrate at one or more indeterminate positions and interfere with the ability of the steam to properly sterilize at that location. The Bowie and Dick test was only a check on the operation of the sterilizer (assurance of adequacy of air removal chamber and packs, and the absence of air leaks in the chamber and steam supply) without a load, and used a specifically-designed challenge, i.e., test pack. Any loading of the sterilizer in addition to the test pack would destroy the reliability of the test. Bowie and Dick test are typically preformed once-a-day on an unloaded sterilizer.

The present invention provides a fully effective substitute for the chemical indicator, paper-based, Bowie and Dick tests, but adopts a different principle of operation. By adopting a different principle of operation, the invention is also capable of operating under full-load conditions to monitor sterilization throughout the day and thereby achieve an even greater degree of safety.

Specifically, the principle of operation of the invention is the collection of air and the measurement of the temperature of the air collected. This is achieved by positioning a heat sink material in a cavity between an opening which permits the entrance of steam and a temperature sensor which measures the temperature of the air collected. Initially the heat sink condenses steam, leaving air in the heat sink. The advancing steam forces the air through the heat sink in the direction of the temperature sensor. As the air passes through the heat sink it becomes cooler than the steam even though it may initially be at the same temperature as the steam by virtue of its contact with the steam and the chamber wall.

The chemical indicator, paper-based Bowie and Dick tests did not depend on the temperature of the air. They depended on the difference in the heating capability between steam and air due to the heat of vaporization. Even though air may be in contact with the steam, the air tends to insulate the heat-sensitive ink from the effects of the steam. As steam with small amounts of air would enter the test packs, the steam would condense. The steam would give up its heat of vaporization and leave behind the air. As more steam would enter the test packs in place of that condensed, condensed steam would be re-vaporized and more would condense and more air in addition to that left behind before would be released. The air would be pushed ahead of the advancing steam front. After a designated period of time, the heat-sensitive ink should have changed color if no air was present. If air had been present, the indicator would not have been heated to the extent necessary and areas of incomplete color change would appear. This color change depends on the calories supplied by the exothermic condensation of steam, not a temperature differential between the steam and the non-condensable air.

None of the prior art electronic systems relate to Bowie and Dick tests or their equivalents. The Joslyn ('893) most certainly does not. First, Joslyn device is used with loads of uncontrolled size and character, contrary to the Bowie and Dick protocol which requires the test to be performed on an empty chamber. Second, the Joslyn system would simply not be capable of the degree of consistency of detection required for a Bowie and dick test in that the device does not provide a controlled challenge to the passage of steam to assure condensation of a sufficient amount to leave behind a detectable amount of air and provides no means for determining if an air bubble exists or might be located. In packs, of the type shown by Joslyn ('893) it is simply not possible to predict where an air bubble might reside. This can be a fatal error.

The test device of this invention, with its heat sink and arrangement of that within a chamber of defined shape in relation to the sensor, enables a result of which the Joslyn ('893) is not capable. The invention achieves its result using elements not taught by Joslyn ('893).

The Apparatus

FIG. 1 illustrates a preferred system of the invention which includes a test device 100 inside the chamber 202 of a sterilizer 200. The test device is shown positioned near drain 204, for obtaining data and transmitting via radio frequency to controller 300 which is shown outside of the chamber 202. The system can operate by obtaining time-temperature data alone or in combination with pressure and/or wet pack (dispersed liquid moisture) data. For each temperature reading, the time that the reading is taken will be recorded to permit calculation of time lags and temperature histories. The data can be transmitted from the chamber by radio, infrared, or ultrasonic transmission or over a hard wire to provide real time monitoring, or it can be stored within the test device 100 for later transmission to controller 300 such as through electrical connection, infrared data transmission, or other suitable means. Whatever means of transmission is selected, a permanent archival record 302 can be generated by display means such as a thermal printer or a chart recorder. This enables accurate records to be kept, whether the system is operated in a mode to perform a Bowie and Dick type test (Bowie and Dick mode) or in a mode to monitor the operation of the sterilizer under load conditions (load mode).

Figure 2:
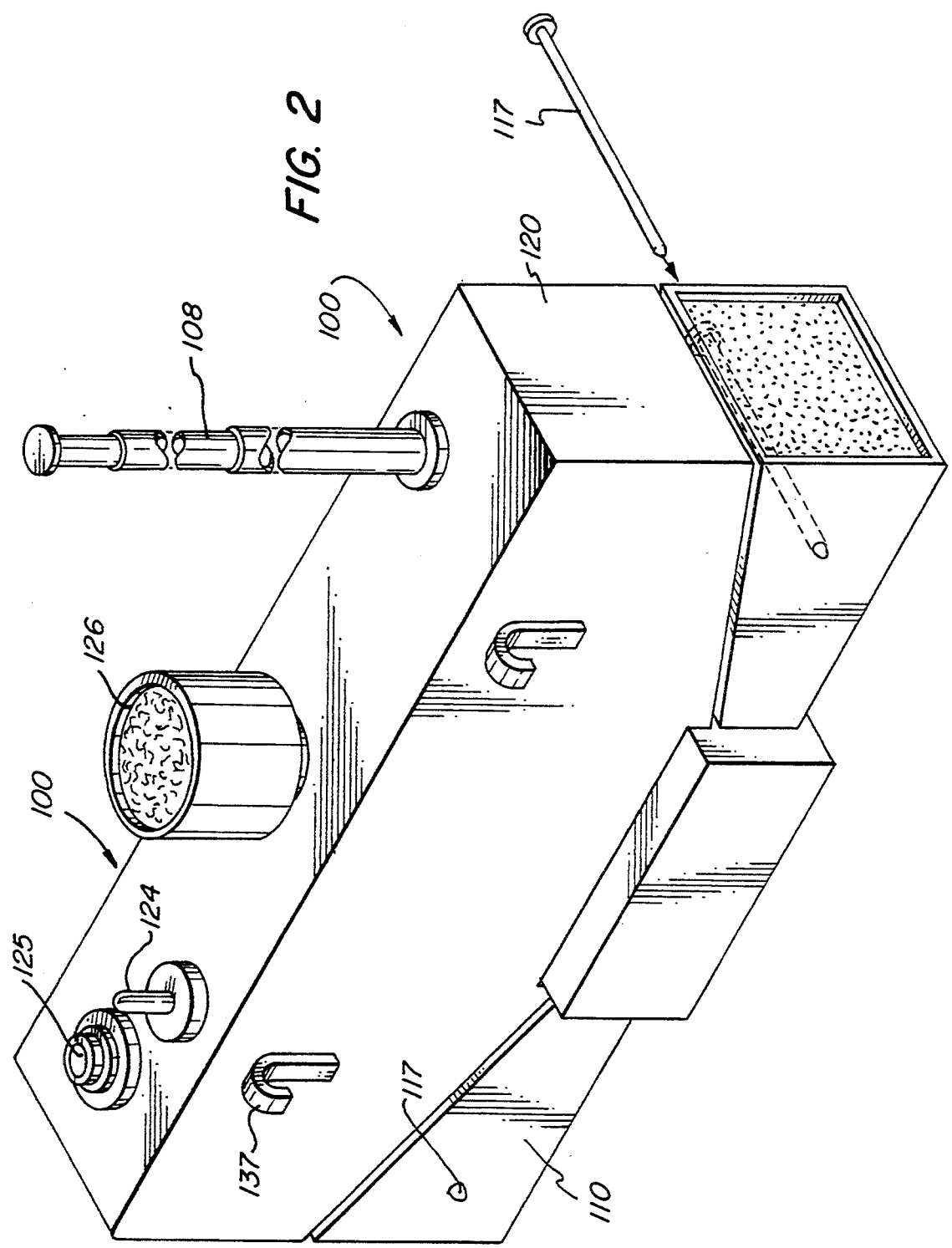
FIG. 2 is a perspective view of a preferred form of test device of the invention.
Figure 5:
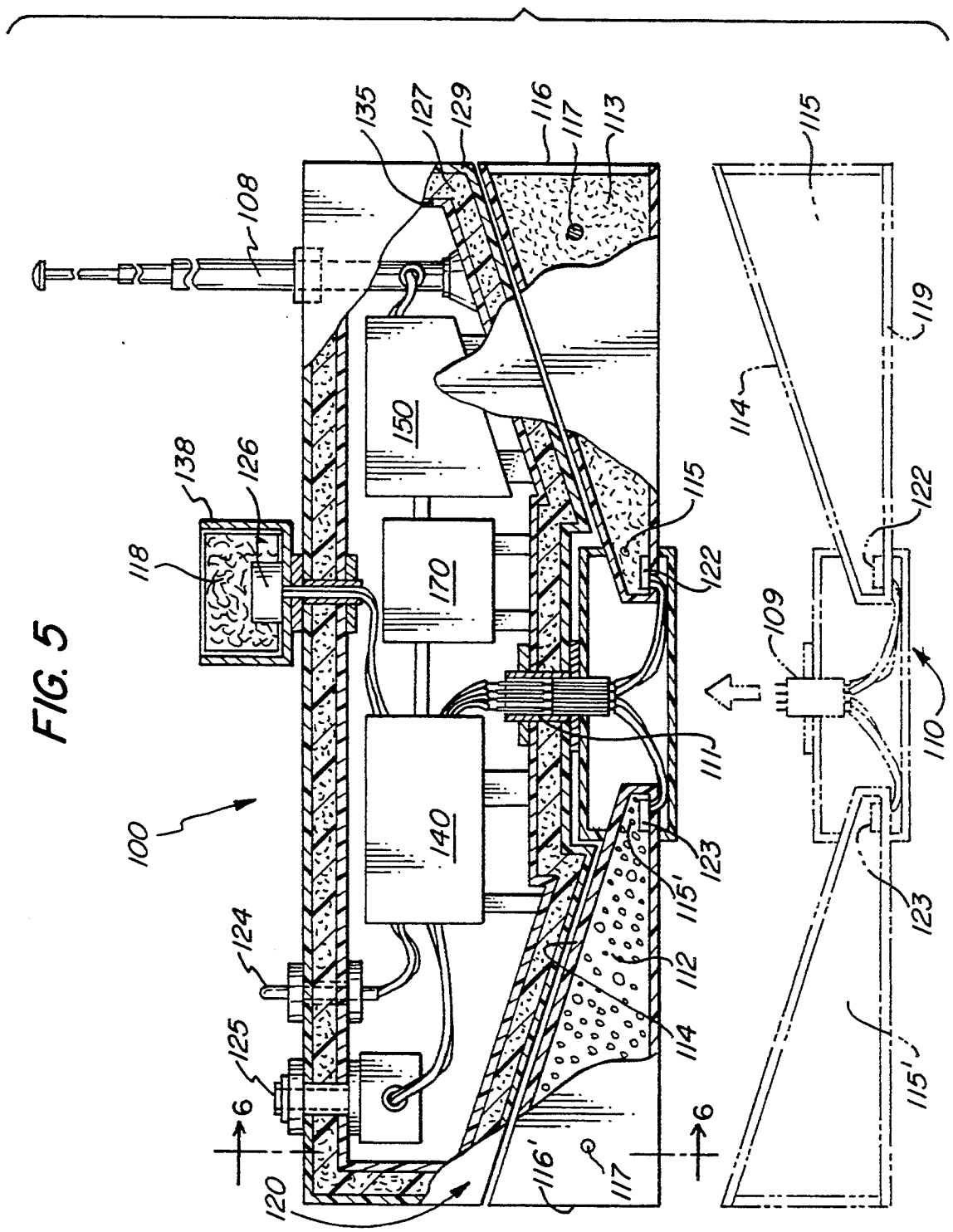
FIG. 5 is a cross-sectional elevation view of the test device shown in FIG. 2, having the back panel cut away to illustrate major components.
Figure 6:
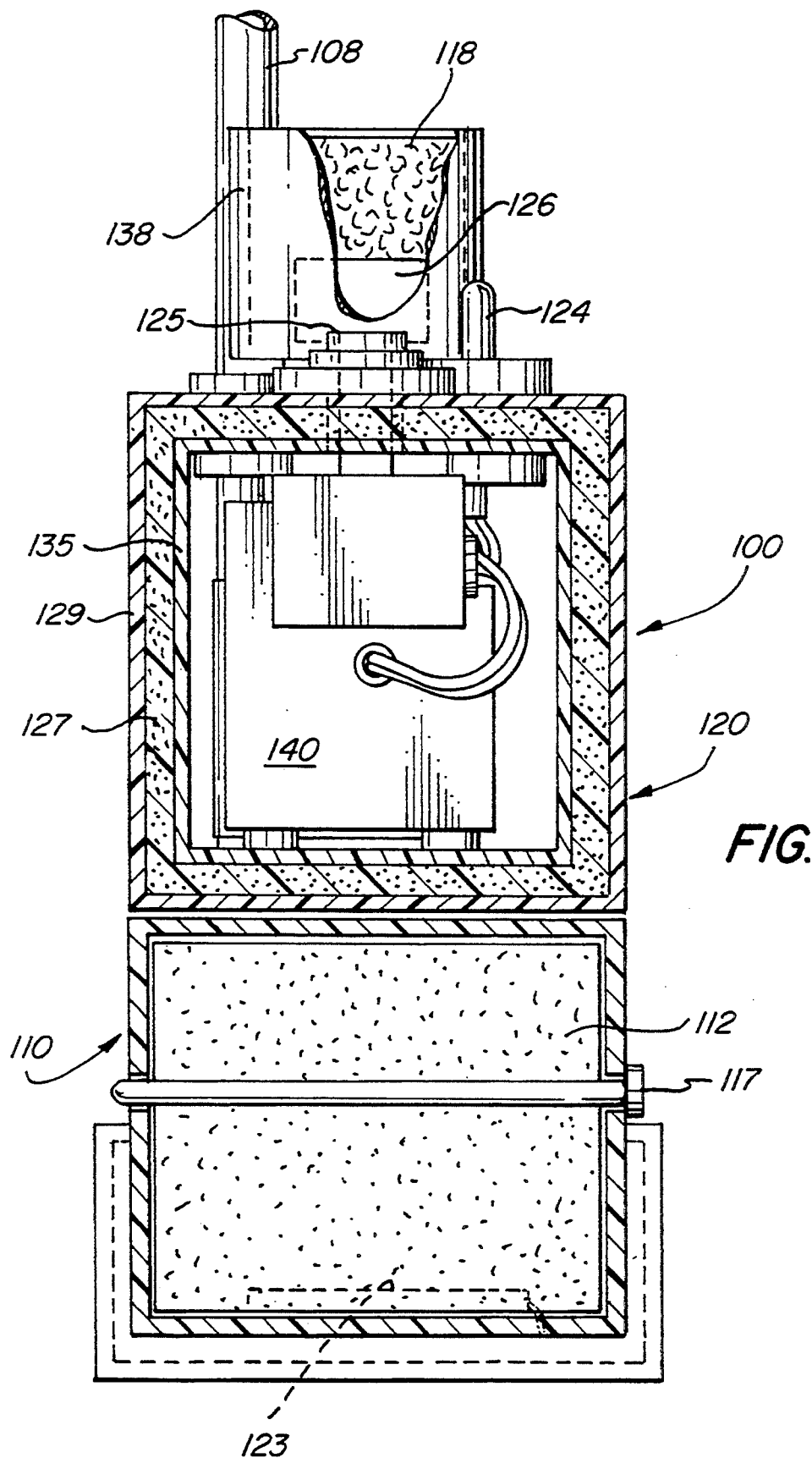
FIG. 6 is a cross-sectional view taken along line 6—6 in FIG. 5.

FIG. 2 shows a preferred form of test device of the invention in greater detail, as do the partially cut away view of FIG. 5 and the sectional view of FIG. 6. The test unit 100 is seen to be comprised of two principal components, illustrated as a replaceable test module 110 and a data acquisition and transmission unit 120. In the embodiment shown, data is transmitted via radio circuitry from transmission unit 120 via antenna 108 as will be described in greater detail below. Preferably, means are also provided to store the data within the test device 100 for later processing. It is also possible to provide a test device such as 100 which is not equipped with radio transmission means, but stores the signals that can be downloaded to the controller at a later time.

Figure 8:
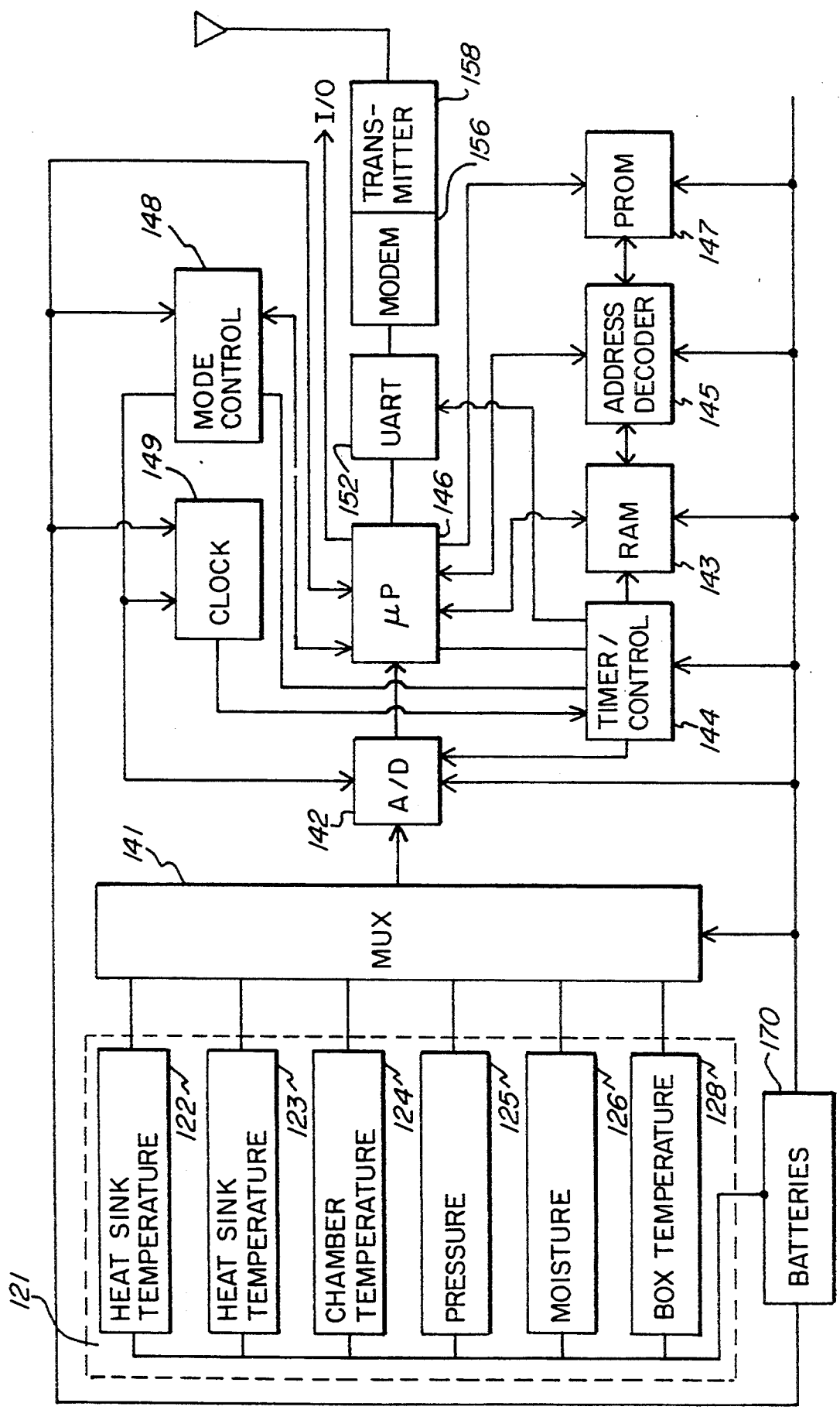
FIG. 8 is a block diagram of the circuitry for a test device such as shown in FIG. 2.

FIG. 8 corresponds to FIG. 5 by showing the major components in block diagram form. Included are all the sensors 121, namely heat sink temperature sensors 122 and 123 in the cavities 115 and 115, covered by heat sinks 113 and 112, temperature sensor for the chamber environment 124 pressure sensor 125, moisture sensor 126, and box temperature sensor 128. Temperature sensors 122 and 123 are preferably thin film Resistant Temperature Detector (RTD) elements, preferably with an accuracy of 0.10° C. in a temperature range −50° to 550° C. such as model EL-700T from HY-CAL Engineering (El Monte, Calif.). They are shown affixed to the bottom of each test cavity close to ends opposite the openings with a high temperature and high thermal conductive epoxy, such as a Coltronic (Brooklyn, N.Y.) product Duralco 4400 adhesive.

In another preferred form of the invention, each test cavity has an array of between three and five RTD temperature sensors affixed in close proximity, but not contiguous along the bottom wall of each test cavity near the closed end so that they can sense the temperature at their different locations.

The temperature sensor 124 is preferably a thin film Resistant Temperature Detector (RTD) element, preferably with an accuracy of 0.10° C. in a temperature range −50° to 550° C. such as model RTS-31 from HY-CAL Engineering (El Monte, Calif.). The pressure sensor 125 is preferably a pressure transducer as shown in FIGS. 5 and 6, such as model P155 from Kavlico (Moor Park, Calif.). The temperature sensors 122 and 123 are shown as component parts of replaceable test module 110. The wet pack detector 126 is desirably embedded within heat sink material 118 in a rack or perforated cup 138 on top of the data acquisition and transmission unit 120. (see FIG. 2) The temperature sensor 128 will be embedded within or closely associated with the temperature-sensitive electronic components, such as 130 within the data acquisition and transmission unit 120. The temperature sensor 128, can be a thermistor capable of generating a signal indicative of the temperature within the transmission unit 120 to warn of overheating.

The temperature sensors 122 and 123 sense the temperature within test cavities 115, 115' located at a position in the sterilizer, usually near the drain 204, where the presence of air is most likely. All of the test devices of the present invention have the capability of obtaining temperature data by sensing the temperatures within a chamber 202 and generating signals indicative of those temperatures.

Figure 7A:
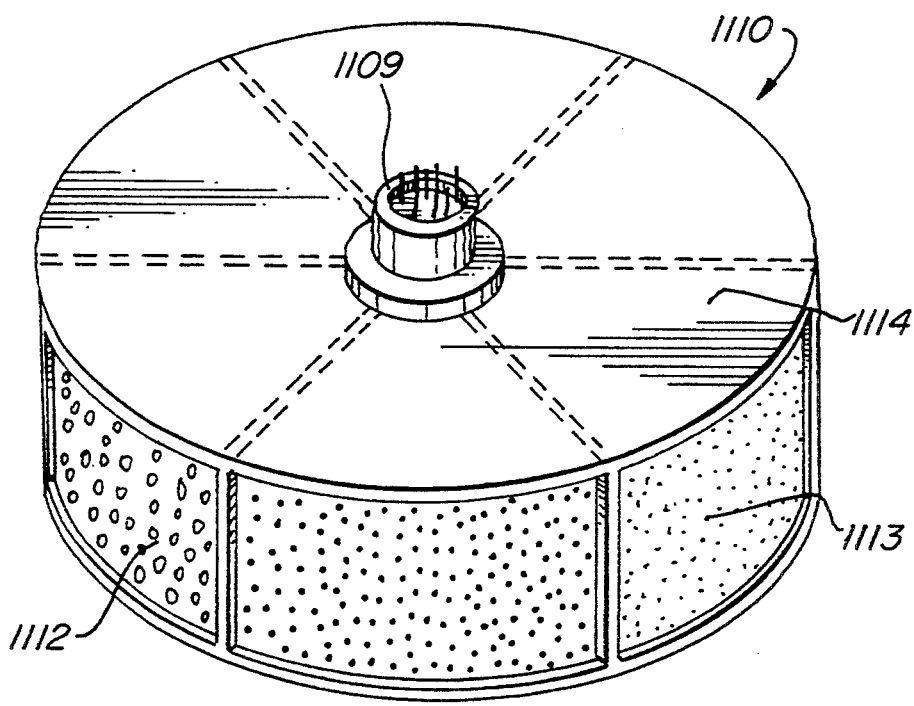
FIG. 7A is a perspective and top view of another preferred form of the replaceable test module of the test device of the invention shown in FIG. 2.

In another of its preferred forms as shown in FIGS. 7A and B, the replaceable test module 1100 comprises wall members defining six elongated test cavities 1115, 1115', etc. arranged in a circle around the connector 1009 having openings 1116, 1116', etc. at one end of each cavity to permit entrance of ambient gases; temperature sensors 1122, 1123, etc., capable of generating signals ($T_1 \ldots T_6$) indicative of the temperatures at their locations at the ends of the test cavities opposite from said openings; and heat sinks 1112, 1113, etc., located in said test cavities between said openings and the ends of the said test cavities; and each heat sink can be of any suitable material which is capable of condensing steam and retaining the condensed steam therein.

Figure 7B:
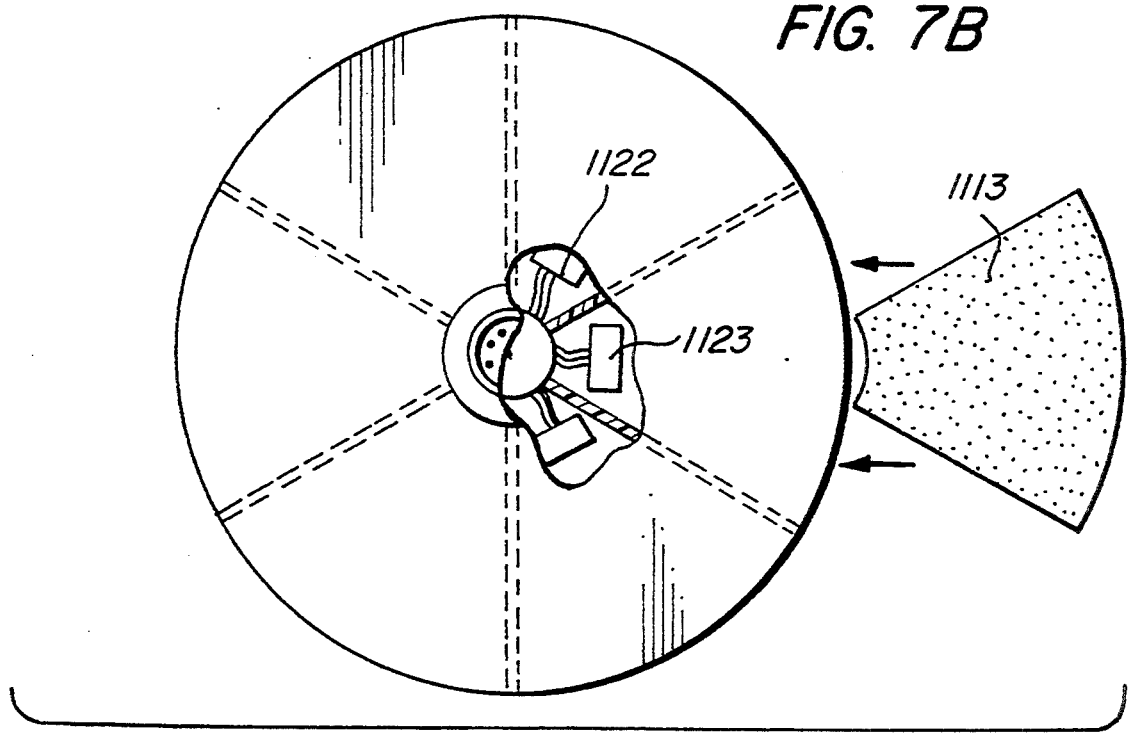
FIG. 7B is a top plan view of the test module shown in FIG. 7A, partially cut away in the top view to illustrate major components.

It is an advantage of a preferred form of the invention that the heat sink material in the various cavities can be different, enabling a range of densities and porosities to appropriately challenge the vacuum system, to make sure air does not leak back into the chamber, and to simulate the kinds of packs, as to density and porosity, that are likely to be found in a loaded sterilizer. One of the cavities' heat sinks should be comprised of material of high density, low porosity so as to provide an appropriate challenge to the vacuum system to make sure residual air is not remaining within the heat sink. The heat sink material in one of the other cavities should be of low density and high porosity so air as a result of leaks within the chamber, vacuum system or steam system will enter the heat sink. All heat sinks should have the thermal conductivity to condense a sufficient amount of steam to cause air, if present, to collect at the end of the test chamber where the temperature sensors are located. The heat sinks are preferably absorbent enough to hold condensed water and, yet, dry rapidly. Gauze or felts of cotton (with or without metallic fibers) should be effective as will standard central supply wrap or open-celled polymer foam. Replaceable test module 1100 as shown in FIG. 7 will connect to a data acquisition and transmission module 1200 similar to the one shown in FIG. 5 but physically shaped to mate with replaceable test module 1100 as shown in FIG. 7.

The pressure sensor 125 is optional, but preferred, and provides the ability to sense the pressure in the chamber environment and to generate a signal which corresponds to it.

The wet pack detector 126, is also preferred, but optional, and adds the ability to sense when packs in the load are going to be wet. Wet packs occur for a number of reasons, including improper loading of the sterilizer, poor steam quality with more than 3% of saturate water by weight entrained in 97% saturated dry steam by weight, and an aborted drying cycle. The wet pack detector is an added advantage of the invention in that it can help identify the causes of the problem and, in the case of where information is being monitored in real time, provide a remedial course of action. The wet pack detector is imbedded in porous material, such as an open-celled foam, that can hold steam condensate and also dry rapidly. The heat sink 118 is held in place on the data acquisition and transmission unit 120 by a rack or perforated cup 138 so as to let excess condensate escape and permit rapid drying. Moisture sensors which measure the presence of liquid moisture suitable for this purpose are such as those described by Smith in U.S. Pat. No. 4,909,070.

In another of one of its preferred forms, the wet pack detector consists of a photoelectric liquid detection method. A Teflon polytetrafluoroethylene encapsulated sensor head is positioned over a porous medium like a muslin pad, that reflects less light when dry and more light when wet, such as occurs in a wet pack condition. The sensor, if activated at the end of the sterilizer's drying cycle, can detect if the pad is wet or has been dried, by the amount of light reflected through it. Such a sensor is available from MEGA (Phoenix, Ariz.).

The replaceable test module 110 in FIG. 5 is designed to concentrate air to the specific locations of the temperature sensors 122 and 123. This module is shown to simply comprise a wall member 114 which defines two elongated test cavities 115 and 115' having openings 116 and 116' to one end to permit entrance of ambient gases, temperature sensors 122 and 123 as described, and heat sinks 112 and 113 fitting and occupying the entire space of the cavity. FIG. 2 shows a suitable means 117, such as a nail, capable of holding the heat sink material in place.

The heat sinks can be of any suitable material which is capable of condensing steam and retaining the condensed steam therein. The heat sink material in one of the cavities should be (e.g., of a higher density, lower porosity material) effective to provide an appropriate challenge to the vacuum system to make sure residual air is not remaining within the heat sink. The heat sink material in the second cavity should be of a different material (e.g., low density and high porosity material), effective to enable air resulting from leaks within the chamber, vacuum system or steam system to re-enter the heat sink. Both heat sinks should have the thermal conductivity to condense a sufficient amount of steam to cause air, if present, to collect at the end of the test chamber where the temperature sensors 122 and 123 are located. The density ratio between the mass of the heat sink material and the volume of the cavity where it is located can be controlled to provide a standard resistance to steam penetration. The heat sinks are preferably absorbent enough to hold condensed water and, yet, dry rapidly. Gauze or felts of cotton (with or without metallic fibers) should be effective as will standard central supply wrap or open-celled polymer foam.

Under conditions of use, the test unit is placed within sterilizer 200 and is subjected to a vacuum before steam is applied. Steam, when introduced, will enter openings 116 and 116' progress into cavities 115 and 115' wherein it will begin to condense in heat sinks 112 and 113. If residual air is present in a heat sink due to inadequacy of the initial vacuum, the air will remain (uncondensed) as the steam condenses around it and be cooled by the heat sink. As this process continues, air, to the extent present in the heat sink, will concentrate at the rear of the respective test cavities 115 or 115' opposite the openings 116 and 116' and insulate the respective temperature sensor from the heat of the steam so that there will be a time lag before the temperature reaches the temperature in the chamber as recorded by temperature sensor 124. If any air is present due to a defective chamber seal, such as seal 208, or leaking vacuum pump or piping, the air will re-enter the heat sinks, especially the heat sink that has low density and high porosity, as the steam enters it and condenses also causing a time lag before the before the temperature sensor reaches the temperature in the chamber.

The length of the time lag can be used to determine the amount of air in the chamber, given certain other available data such as the chamber size, the temperature of heat sink, the density ratio between the mass of the heat sink and the volume of the cavity where it is located. Generally, the longer the time lag, the more air there is in the chamber.

If a replaceable test module with array of temperature sensors is employed, a volume of air in the cavity, to the extent present, can be determined by equating it to the volume of the cavity with one dimension determine by the furthest point from the end the cavity where there is air as determined by a time lag on one of the temperature sensors in the array affixed along the bottom wall of the cavity.

If the steam is too wet, containing more than 3% saturated water by weight to the weight of dry steam, this could cause wet loads which are difficult to dry and are more easily re-contaminated and may interfere with obtaining effective temperature readings. It is therefore desirable to employ a wet pack detector 126.

The replaceable test module 110 is desirably in cartridge form which can simply be snapped into and out of position (see FIG. 5), using a connector that has the mechanical strength to withstand numerous connections and disconnections while providing support for the test module 110 and is able to withstand the harsh environment. Such a sealed non-latching panel plug, model SFE 104 A066-60 made by W. W. Fisher (Atlanta, Ga.) can be used for the test module 110. It can plug into a the appropriate sealed panel receptacle in the data acquisition and transmission unit 120 such as DEE 104 A066-60 from the same company. It is recommended that these modules be replaced periodically, e.g. weekly or monthly. Whenever subjected to excessively wet steam, they should be allowed to dry before being used. When employed in the load mode to monitor the conditions during sterilization, the cartridges may be changed after each cycle to assure that a dry cartridge at room temperature is present at the start of each run. These cartridges may be reused several times. In one embodiment, it is desirable to provide means for preventing operation of the unit in the load mode unless the cartridge has been replaced.

Another feature of the cartridge is the provision of bottom wall 119 which slopes away from the sensors to prevent liquid water from collecting at that location. When placed on a level surface, liquid water flows toward openings 116 and 116'.

Referring again to FIG. 5, the data acquisition and transmission unit 120 is shown to have an outer casing 129, an inner casing 135 with a layer of insulation 127 between the two cases. After the insulation is in place and the external and internal cases are air tight, a partial vacuum is drawn (e.g., to 0.5 to 10 inches of mercury or on the order of one commonly found in thermos bottles). The case can be injection molded using a high performance plastic resin, such as General Electric ULTEM polyetherimide resin that has a heat deflection temperature of 392° F. at 264 psi. The insulation can be polyurethane foam at 2 lbs. per cubic foot. The casing and insulation together should provide temperature protection for the sensitive internal components up to at least about 290° F., a vacuum of less than one-half inch of mercury and a pressure differential of at least 5 atmospheres. The transmitting antenna 108 is a length of $\frac{1}{4}$-wave wire located perpendicular to the base of casing 129 which acts as a ground plane.

When the sterilizer is being monitored actually loaded and being used to process materials, the test device can be hung on the side of the sterilizer cart racks using hooks 137 on the test unit 100 so as to be out of the way and not take up space that could be occupied by an other pack. The test unit can also be placed flat on the sterilizer cart trays.

Transmission of the data is effected by unit 150 shown in FIGS. 5 and 8 which includes UART 152 (universal asynchronous receiver-transmitter), modem 156 and radio transmitter 158. Specifically, the UART can be an Intersil 6402 unit and the modem and transmitter can be combined as in an FM unit such as a Motorola RNet 9600 series manufactured by Motorola Inc. Radius Division, Schaumberg, Ill., which transmits at 464 MHz FM with a frequency deviation of 7.5 KHz. Power is preferably provided by a battery pack 170, preferably rechargeable.

FIG. 5 shows, in addition to the transmitting unit, a signal processing unit 140 and a battery unit 170. The signal processing unit 140 can be seen from FIG. 8 to preferably include a multiplexer 141 which receives the signals from the sensors 121 and distributes them as called for, an analog to digital converter (ADC) 142 which digitizes the analog signals from the multiplexer, and a timing and control unit 144 which also receives a clock input from clock 149. The times at which each temperature reading is taken is recorded to permit time lags and temperature histories to be calculated and referenced by the microprocessor 380 in the controller.

FIG. 8 illustrates a microprocessor 146 which has programmable read only memory (PROM) 147 and random access memory (RAM) 143 connected to an address decoder unit 145. The microprocessor with its associated memory can be employed to enable storage of digitized signals from the sensors for transmission to the controller or other signal processor only after removal from the chamber. To facilitate this type of transfer, a hard data link can be established by utilizing 4 pins on the female receptacle connector 111 used between the test module 110 and the data acquisition module 120 and a male plug 310 on the control unit can be provided to electrically couple the two units. Alternatively, other data transmission means, including those based on infrared and ultrasonic transmission, can be employed.

As also indicated in FIG. 8, there is a mode control unit 148 connected to the Timer/Control 144 and the microprocessor 146 to control power to the sensors and the transmitter in order to conserve power by utilizing low power through out. For example, until a temperature within the sterilizer is equal to or greater than a designated temperature ($T_o$) for powering up the sensors, the device will be in sleep mode. At a designated time and temperature the transmitter will be powered up to send data to the external controller 300. Similarly, the same sequence can be followed to shut down the unit when the temperature drops below $T_o$. Also the unit can be shut down and a warning given when the temperature exceeds a preselected upper value.

Figure 3:
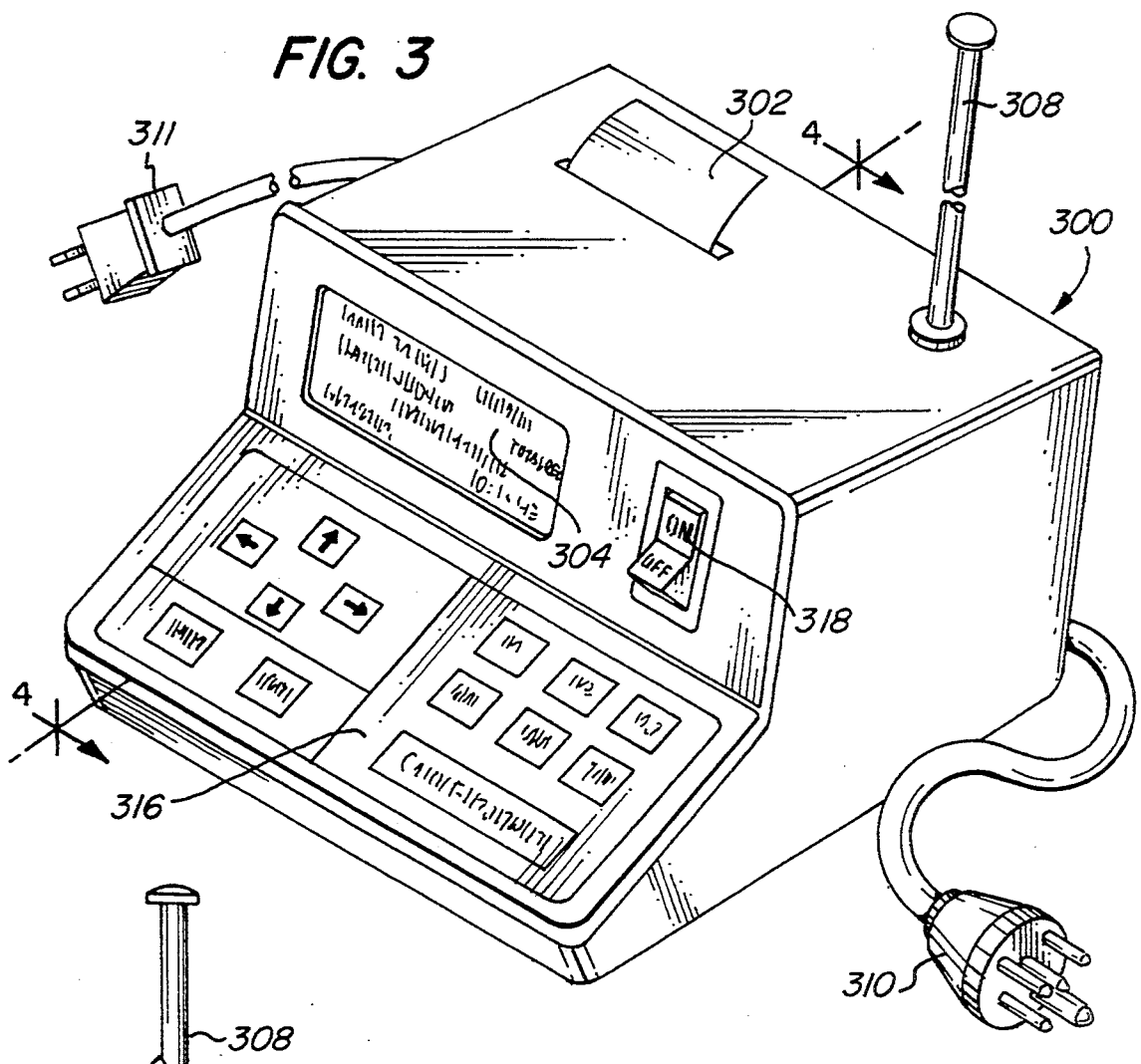
FIG. 3 is a perspective view of a preferred form of controller unit of the invention.
Figure 4:
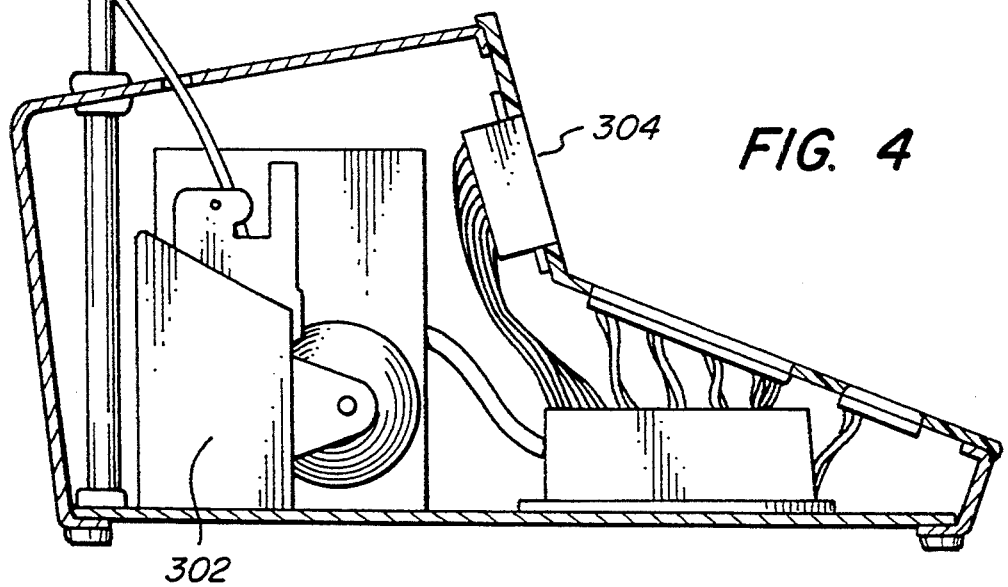
FIG. 4 is a cross-sectional elevation view of the controller unit taken along line 4—4 in FIG. 3.
Figure 9:
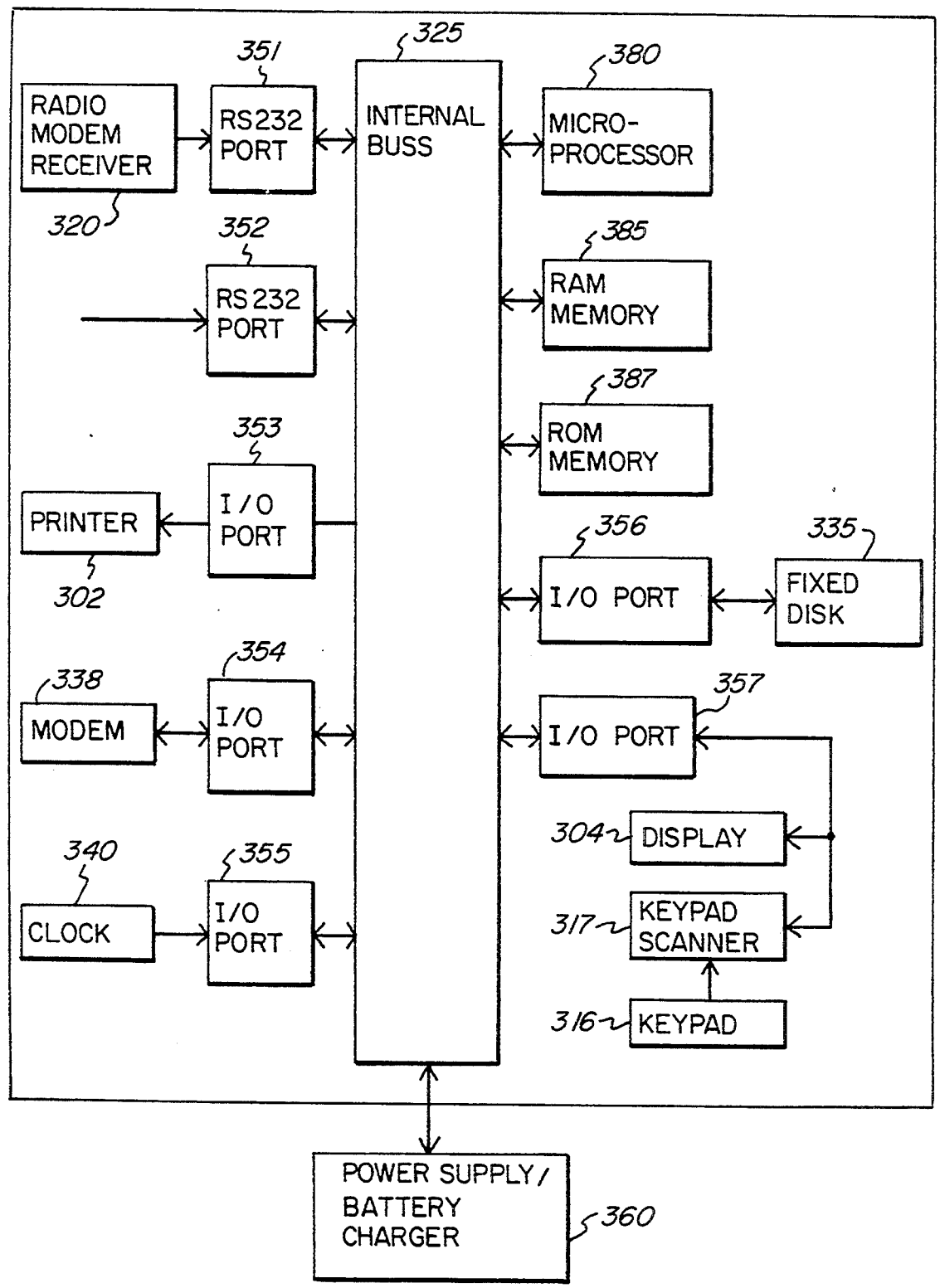
FIG. 9 is a block diagram of the circuitry for a controller unit such as shown in FIG. 3.

FIGS. 3 and 4 show the principal components of a preferred controller 300 according to the invention, and FIG. 9 shows the arrangement of the components in a block diagram. The controller can print the test results on a thermal printer 302, such as model LTP 5442-832 from Seiko Instruments (Torrance Calif.) in any desired format and can provide real time indication of conditions on a liquid crystal display (LCD) 304. Data on the conditions inside the steam sterilizer chamber is received preferably by radio, employing antenna 308. Alternatively, as discussed above, the data can be transmitted after the data and acquisition and transmitter unit is removed from the sterilizer through a wired data link employing male plug connector, like the one 109 used with test module 110. The face of the controller is also shown to include a 128×64 dot LCD display 304 such as model G1216 from Seiko Instruments (Torrance, Calif.) which provide visual warning of a wet condition in the sterilizer and confirmation of effective reception of transmission from the transmission unit.) Power can be provided from standard current through line 311 to an internal power source that can also serve as the battery charger for the data acquisition transmission module 120.

The face of the controller has an on/off switch 318 and a membrane keyboard 316 as could be supplied by Topflight Corporation (York, Pa.).

FIG. 9 is a simplified block diagram of the controller 300. As shown an internal buss 325 is utilized, with the data acquisition and transmission unit interface being provided through RS 232 port 351 leading to radio modem receiver 320 (for receiving sensed data from the data acquisition and transmission unit 100) or RS 232 port 352 if the data acquisition and transmission unit 200 is downloaded to the controller 300 through a hard wire 310. In addition, internal buss 325 of controller 300 is also connected with I/O port 357 leading to display 304, keypad scanner 317 which connects to keypad 316 (data, such as type of cycle, can be input by an operator with the key pad); I/O port 353 leading to printer 302 (to generate printed reports), I/O port 354 leading to modem 338 (for optional down loading of software revisions), I/O port 356 leading to fixed disk 335 (to store programs and data base), I/O port 355 leading to clock 340, microprocessor 380, RAM memory 385, ROM memory 387. Power supply/battery charger 360 is provided to supply power to controller 300 and is able to charge the batteries in the data acquisition and transmission unit 120.

In its preferred form, the system will be capable of operation in at least of two modes: (1) a Bowie and Dick test mode, typically run once a day (e.g., each morning) on an empty sterilizer only temperature readings are important, and (2) a test under load.

In the case of the Bowie-Dick-type test, a single pack (the test pack) is placed in the chamber; to the extent present, air in the chamber will concentrate in this single pack for maximum detection (the small-load effect), but when other packs are in the chamber, air, to the extent present, may be divided among them unequally. The reference temperatures used for the Bowie and Dick type test can not be used in the load mode because of the small-load effect, whereby air, to the extent present, tends to concentrate in the single pack. The particular reference temperatures will differ depending on whether or not a load is present and the kind cycle that the operator has chosen to run (typically, a sterilizer is set for one kind on cycle that will sterilize all kinds of loads, but it might be set for processing instruments, for example, that can have a shorter cycle) the kind of load and the particular sterilizer.

Accordingly, the controller must be set for the particular mode for each cycle of operation and the kind of cycle that is being employed. When the mode is set, the appropriate program will present the reference conditions for that mode, sterilizer and particular load. The load mode reference conditions will typically be unique to an individual sterilizer. They will be generated by a "Small Load Compensator Program" that is able to estimate the amount of air (the dependent variable) that should be in a sterilizer chamber depending on the value of a number of independent variables including, but not limited to, the kind of sterilizer, the manufacturer, the size of the chamber, the maximum number of packs that can be processed, the current number of packs, the size of the packs, the kind of packs, exposure time and temperature, the amount of air present in the last successful Bowie & Dick Test.

A number of statistical methods such as multiple regression analysis can be employed for this purpose. In its preferred embodiment the invention uses a neural network computing software program manufactured by NeuralWare, Pittsburgh, Pa. There are application programs for 386-type microprocessors, such as used in controller 300. The neural network can learn of its own accord from a dynamic system to provide better reference temperatures.

Figure 13:
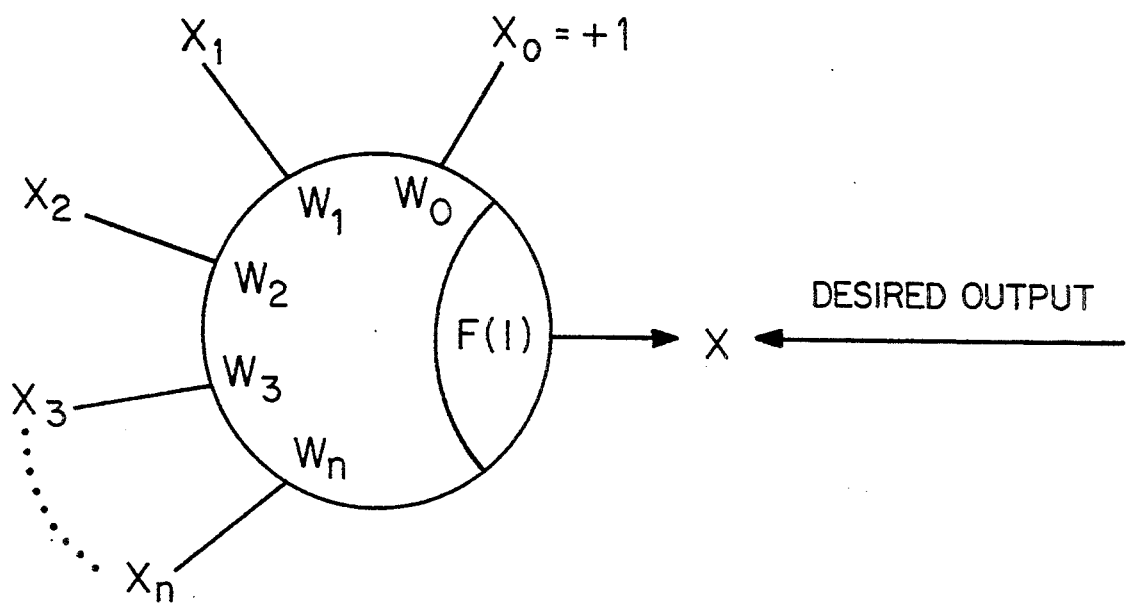
FIG. 13 is a chart depicting the basic building block of a neural computing network, the "neuron," and the formula to represent it.

A neural network program has inputs and outputs and is composed of many simple and similar processing elements. In FIG. 13, the "X" values are inputs or independent variables. The "Y" value is the output or dependent variable. The "W" values are weights and are analogous to regression coefficients in a linear regression equation.

During the "training" or adaptive process, the output of the processing element is computed from the formula shown in FIG. 13. This is compared to the desired output, and the weights are adjusted as needed to make the actual output ("Y") correspond to the desired output.

Some of the inputs, the independent variables, are the environmental conditions being sensed by the test 100; other inputs are supplied from a data base that has been pre-loaded into the controller 300. The data base information will include chamber sizes for sterilizer manufacturers' different models, the exposure times and temperatures for different cycles, etc. Initially, before putting the unit into service, the operator will need to enter identifying information, such as model or serial number, for the particular sterilizer being monitored, so the pre-loaded data base information can be loaded into the neural network software program. The operator needs to enter additional information for each loaded cycle, such as the number of packs in the load. In a typical configuration, the operator can enter this information by selecting items from a simple menu. Such a menu for imputing the number of packs in the load would look like this: Select A, B, C, or D that best describes the number of packs in the current load: A. 1 to 3 B. 4 to 7 C. 8 to 11 D. 12 or more The controller can be equipped to receive reference temperature, pressure and moisture data by a trained operator, periodically, as new versions of the software become available, via data link such as modem 338.

To assure that the proper mode of operation and correct information has been selected by the operator, a display will show a message on display 304 indicating the mode or information selected and ask the operator to confirm it by pushing the "CONFIRM" key on the keypad 316. For instance if the operator has selected from a menu the number of packs in the load as 4-7, the display might read:

THE CURRENT LOAD HAS BETWEEN 4 TO 7 PACKS IF THIS IS CORRECT, PRESS CON-

FIRM KEY TO ENTER A DIFFERENT NUMBER OF PACKS, PRESS RESET KEY

The controller preferably includes means which prevent the test cycle from beginning and any report to be printed until the "CONFIRM" key is activated.

The Principal Methods

Figure 10:
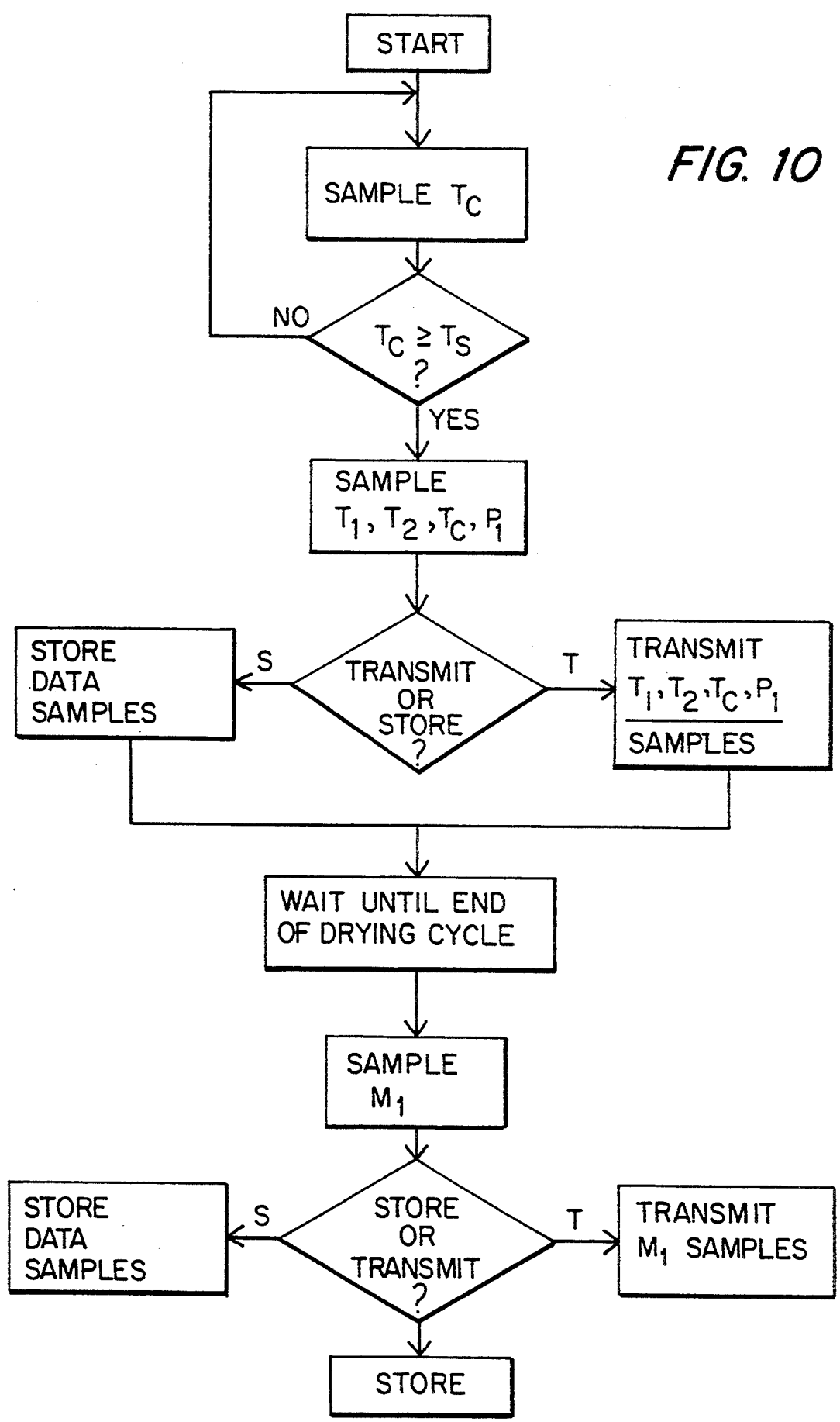
FIG. 10 is a flow-chart depicting the operation of a preferred test device according to the invention.
Figure 11:
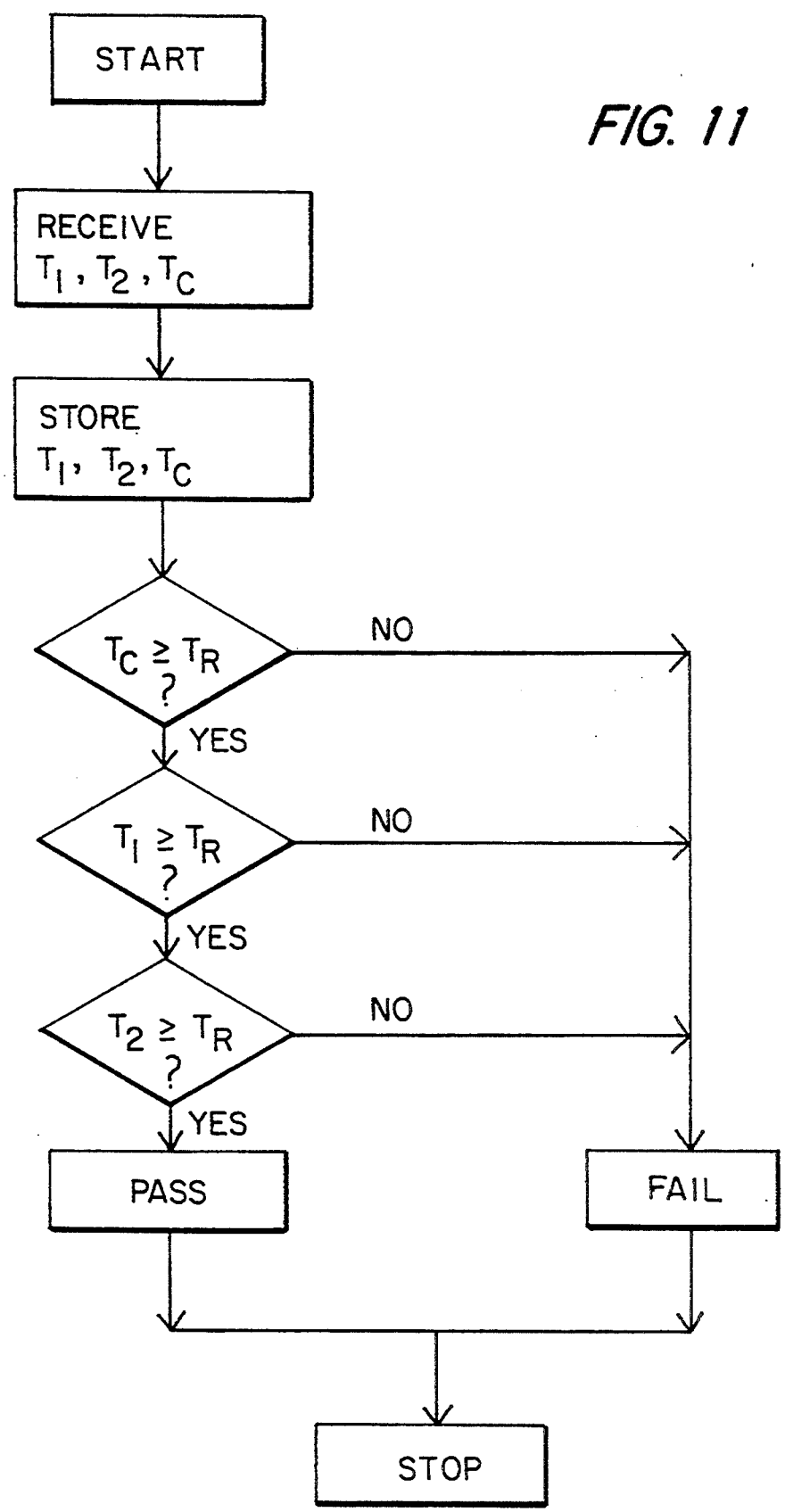
FIG. 11 is a flow chart depicting the operation of a preferred controller unit in the Bowie and Dick mode of operation according to the invention.
Figure 12:
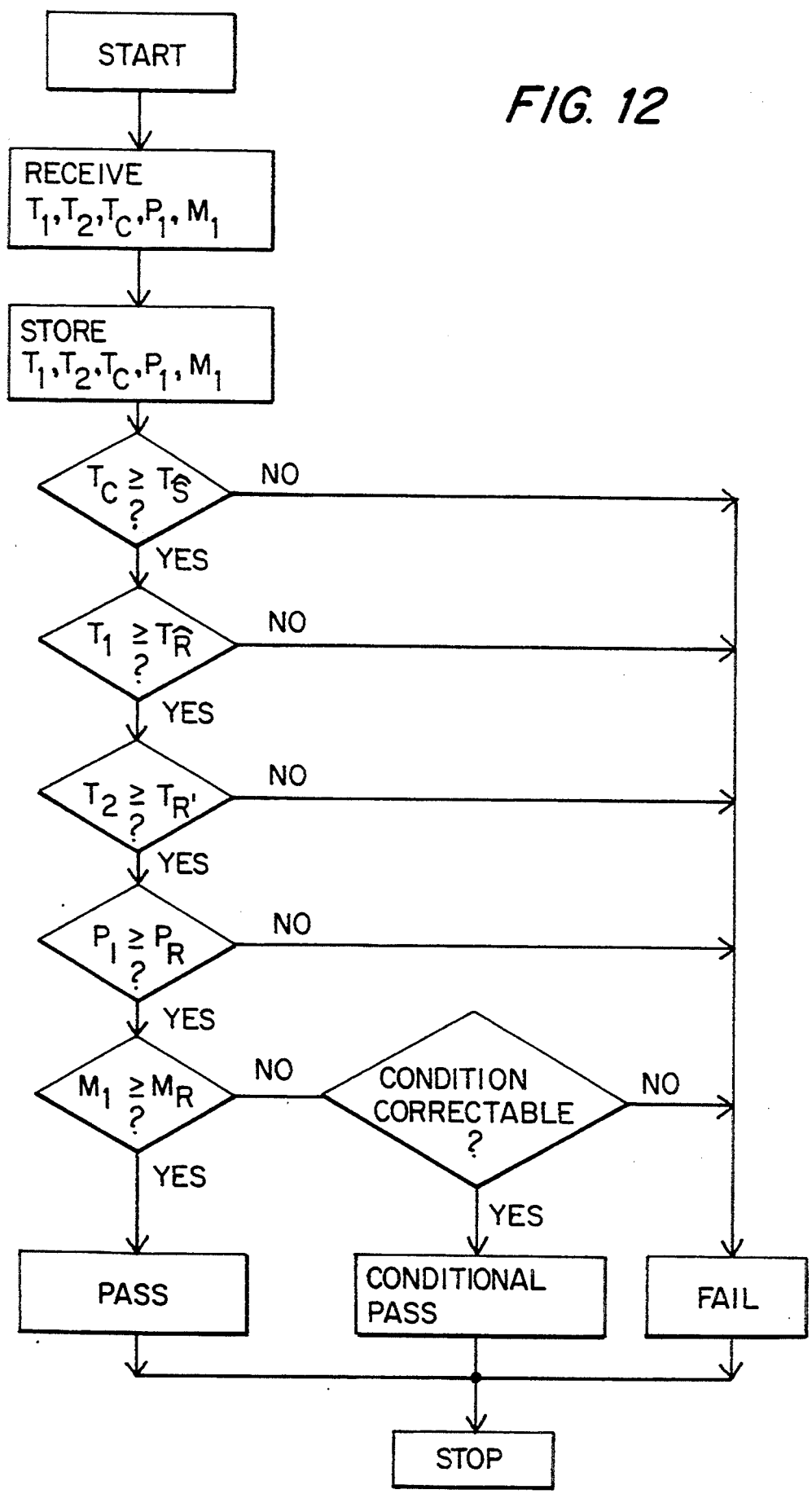
FIG. 12 is a flow chart depicting the operation of a preferred controller unit in the load mode of operation according to the invention.
Figure 14A:
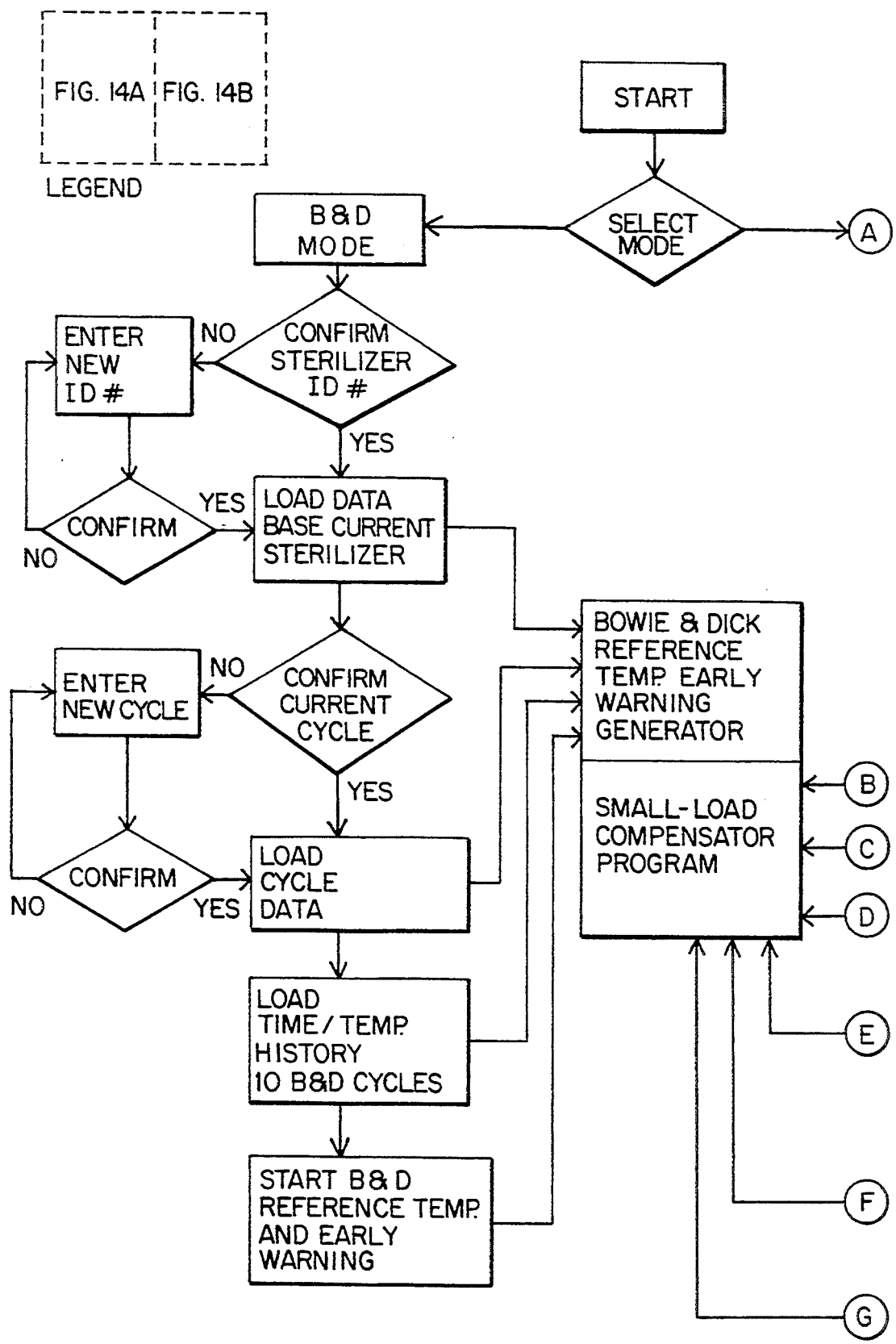
FIGS. 14A and 14B together provide a flow chart showing how selecting the "mode" of operation activates the programs to generate the reference temperatures.

The operation of a preferred system can be followed by viewing FIGS. 10, 11, 12 and 14A and B. FIG. 10 is a preferred flow diagram for the operation of a test device 100, and FIG. 11 is a preferred flow diagram for the operation of a controller 300 in the Bowie and Dick Test Mode; FIG. 12 is a preferred flow diagram for the operation of a controller 300 in the Load Mode; FIGS. 14A and B depict a flow diagram for the preferred operation of controller mode setup.

Bowie and Dick Mode

FIG. 14A and B define a flow diagram showing how the mode is set in order to generated the correct reference temperatures. In one preferred Bowie and Dick mode operation, a sterilizer having a preliminary vacuum cycle is opened and the test device 100 is placed therein. The sterilizer cycle is then begun, and a vacuum is drawn for the designated period of time. This is followed by the introduction of steam at a designated temperature (e.g., 270° F.) for a designated time (e.g., 4 minutes). The test unit continuously monitors the time/temperature. Analog data from this and other transducers is continuously digitized and presented to the microprocessor.

When the chamber temperature $T_c$ (sensed, for example, by sensor 124) reaches $T_o$, a preselected temperature a few degrees below the exposure temperature for the particular sterilizer, the test device is turned on to collect and store test time/temperature values, ($T_1, T_2 \ldots T_n$)) and $T_c$. Temperature $T_1$ and the signal generated are indicative of the temperature at the location of temperature sensor 122 in cavity 115. Temperature $T_2$ and the signal generated are indicative of the temperature at the location of temperature sensor 123 in cavity 115'. Temperature $T_n$ and the signal generated are indicative of the temperature at the location of temperature sensor (n) in cavity (n).

The controller 300, or functional equivalent, preferably receives transmitted test data and processes it in accordance with FIG. 11. The controller receives and stores data indicative of $T_1, T_2 \ldots T_n$ and $T_c$, and then compares signal $T_1, T_2 \ldots T_n$ and to a stored signal $T_r$ which is typically the intended sterilization temperature. Stored within memory is reference time/temperature information, and a signal $T_r$ is generated indicative of this reference temperature. The reference time/temperature can be a predetermined time/temperature, e.g., 4 minutes at 270° F., or a calculated value based on a computed average of selected values from earlier runs, e.g., the last ten Bowie and Dick mode time/temperatures.

Load Mode

Figure 14B:
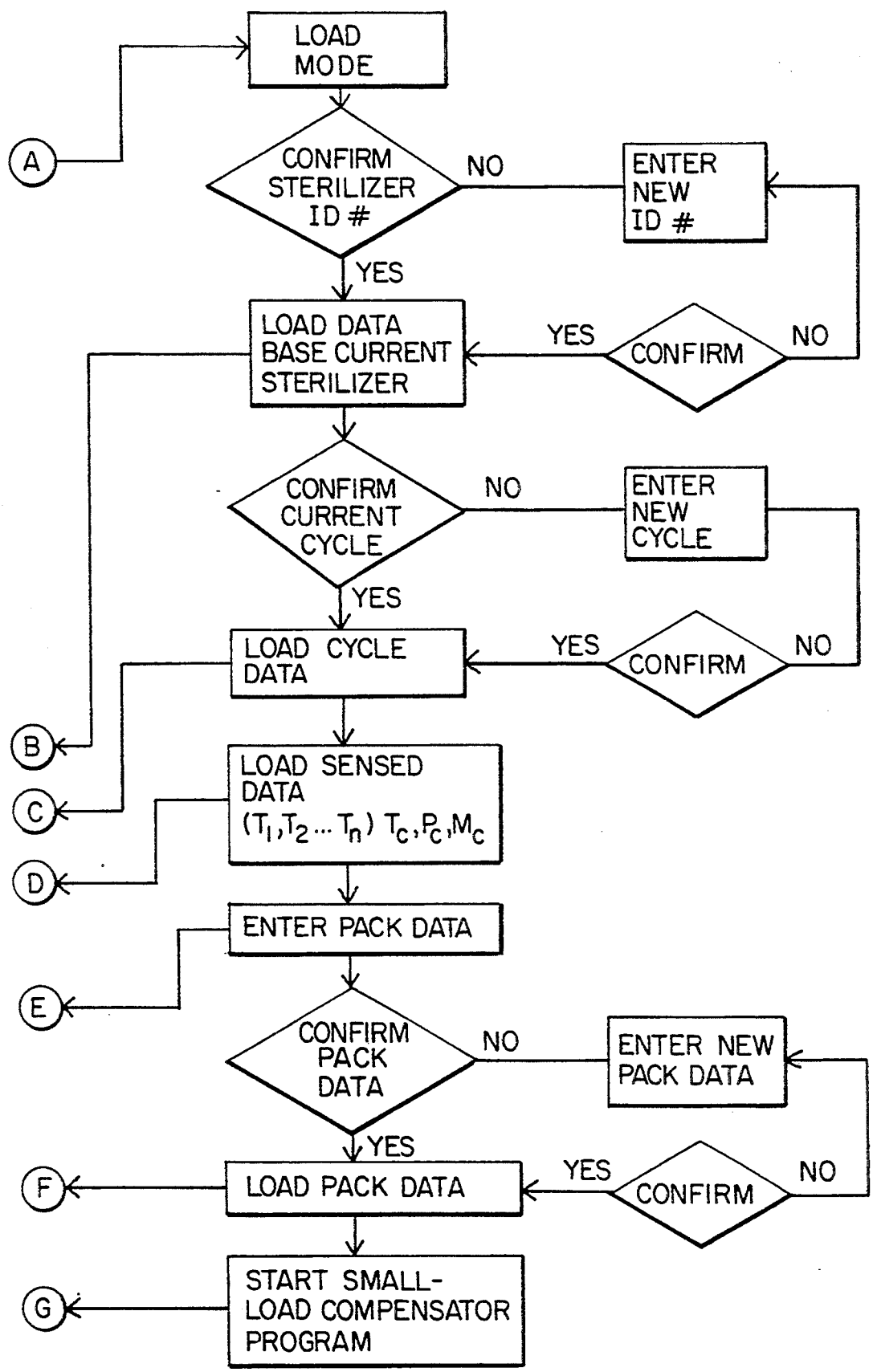

In the load mode, various packages undergoing sterilization will be located within the sterilization chamber. The reference temperature will depend on the kind of cycle that the operator has chosen to run, the kind of sterilizer and the kind and size of the load. The reference time/temperatures for the load mode will be generated by the Small-Load Compensator program using the aforementioned information; see FIG. 14 for a flow diagram for setting up the load mode.

Accordingly, the controller must be set for the particular mode for each cycle of operation and the kind of cycle that is being employed. The operator, using the key pad and following prompts on the display needs to enter additional information for each loaded cycle. After this step has been completed the appropriate program will present the reference conditions for that mode, sterilizer and particular load.

In one preferred load mode operation, a sterilizer having a preliminary vacuum cycle is opened, loaded and the test device 100 is placed therein on one of the racks or hung on one of the racks near the drain. The operator selects the mode, the cycle and enters the specific load information. Then the sterilizer cycle is then begun, and a vacuum is drawn for the designated period of time. This is followed by the introduction of Steam at a designated temperature (e.g., 270° F.) for a designated time (e.g., 4 minutes). When the chamber temperature $T_c$ reaches a designated $T_o$ value, the test device is turned on.

The test device continuously collects the time/temperature, and pressure data. Analog data from the sensing elements is continuously digitized and presented to the microprocessor to transmit or store temperature values, $T_1, T_2 \ldots T_n$ and $T_c$ and pressure value $P_c$. Temperature $T_1$ and the signal generated are indicative of the temperature at the location of temperature sensor 122 in cavity 115. Temperature $T_2$ and the signal generated are indicative of the temperature at the location of temperature sensor 123 in cavity 115'. Temperature $T_c$ and the signal generated are indicative of the temperature at the location of temperature sensor 124. Pressure $P_c$ and the signal generated are indicative of the pressure at the location of the pressure sensor 125.

After the drying cycle has been completed (determined by either elapse time in the cycle, temperature and or pressure readings), the test device collects moisture data. Analog data from the sensing element is continuously digitized and presented to the microprocessor to transmit or store value, $M_1$. Moisture $M_1$ and the signal generated are indicative of the moisture at the location of temperature sensor 126.

The controller 300, or functional equivalent such as a 386 personal computer equipped with a radio modem receiver and thermal printer, preferably receives transmitted test data and processes it in accordance with FIG. 12. The controller receives and stores data indicative of $T_1, T_2 \ldots T_n$, $T_c$, $P_c$ and $M_c$. The controller first compares $T_c$ with the exposure time/temperature for current cycle to be sure these parameters are correct. If they are, then the controller compares signal $T_1$ and $T_2$ to a signal $T_r$ a reference time/temperature, which is generated by the "Small-Load Compensator Program", displays a pass or fail message on the LCD display 304 and issues a printed report on the thermal printer 302.

If this test is meet, the controller then compares pressure $P_c$, to $P_r$ indicative of a reference pressure. The reference pressure can be a pressure obtained from stored steam table information to indicate the pressure for saturated steam at the temperature specified for the current cycle or $T^c$, the actual temperature, with or without a designated tolerance. For example, the signal $P_c$ can take into account a permissible 5° or 10° F. degrees of superheat. In other words $P_r$ can be slightly higher than the value for saturated steam at $T_c$.

After comparison for temperature, and if desired, pressure, the controller's database containing, among other information, the sterilizer's specifications is queried to find out the length of the drying cycle, the start of which can be identified by temperature and or pressure readings. (logic is queried to assure that the test time, or shorter time for the comparison, has not expired.) After the drying cycle has finished, moisture data can then be taken and compared to a reference moisture point, and a message included on the display or printed report regarding the sterilization conditions. If the comparison indicates, that the moisture level is higher than it should be, a wet pack condition probably exists.

THE SECONDARY METHODS

Early Warning

It is desirable to know in advance if the sterilizer is going to fail at some point in time, so preventive action can be taken to minimize downtime. In the preferred form, the system will be capable of providing an "Early Warning" of possible failure. This warning can be generated by storing past test results, and then, after first including the current Bowie and Dick test results in this set, performing a trend analysis to determine if the test results are following a trend toward a failure. A message indicating this status can be printed along with the results of the Bowie and Dick test that will need to be kept as a permanent record.

Remedial Action

If the wet pack condition is not sever, it is possible to extend the drying cycle and dry the packs in the sterilizer. Moisture points higher than the reference moisture point can be correlated to additional drying times. (e.g., one point higher means two minutes of additional drying time; two points higher means three and one-half minutes of additional drying time, etc.)

Fault Diagnosis

It is also desirable to know the sources of a failure in the sterilizer. In its preferred form the system can provide indications of the source of the problem. For instance, in the Bowie and Dick mode, if the vacuum pump is at fault, the temperature sensor associated with the heat sink that has high density and low porosity will show a greater temperature lag than the temperature sensor associated with the heat sink that has low density and high porosity. If, on the other hand, the fault is a result of air leaking into the chamber after the initial vacuum has been drawn, the temperature sensor associated with the heat sink having low density and high porosity will show a greater temperature lag than the temperature sensor associated with the heat sink having high density and low porosity. A message can be displayed or printed to identify the source of the problem, either a poor initial vacuum or an air leak.

In the load mode, if any sterilization condition has been identified not favorable to a successful sterilization process, the monitor can use the sensed data to diagnose the possible cause of the condition. The three major problems are air in the chamber, super heat, and wet packs. Air in the chamber results from either a vacuum fault or an air leak. If the vacuum pump is at fault, the temperature sensor associated with the heat sink that has high density and low porosity will show a greater temperature lag than the temperature sensor associated with the heat sink that has low density and high porosity. If, on the other hand, the fault is a result of air leaking into the chamber after the initial vacuum has been drawn, the temperature sensor associated with the heat sink having low density and high porosity will show a greater temperature lag than the temperature sensor associated with the heat sink having high density and low porosity. A message can be displayed or printed indicating the appropriate cause of the problem.

Wet packs, can be caused by excessive water entrained in the steam, (e.g., more than 3% of saturated water by weight entrained in 97% saturated dry steam by weight), steam that is alternately at pressures below the saturation pressure for the correct exposure temperature, incorrect packaging and incorrect loading of the sterilizer. If pressure and temperature readings are within the appropriate limits, and the moisture level is above the reference moisture level, a message will be displayed and/or printed indicating a wet pack condition is likely because the steam has excessive water entrained in the steam. If the moisture level is above the reference moisture level and pressure has been below the reference pressure during the exposure period, the cause of the a wet pack condition could be caused by excessive water entrained in the steam or poor steam quality in terms of pressure.

If moisture, pressure. and temperature reading are satisfactory and the packs are wet when the sterilizer door is opened, it is likely that the wet pack condition can be attributed to incorrect packaging, loading of the sterilizer, or both.

Using the time/temperature readings can determine if the sterilizer has been loaded correctly. If the temperature lag "Small Load Compensator Program" expects to measure is more than the readings returned by both $T_1$ and $T_2$, a message will be displayed and/or printed indicating that the sterilizer might be loaded incorrectly and thus not be able to sterilize the packs. Thus, the invention provides a method for determining if the sterilizer has been loaded correctly, comprising:

placing a test device capable of sensing at least two temperatures within the chamber of a sterilizer, indicative of two of the most frequent faults, the inadequacy of the initial vacuum and air leaks in the chamber, vacuum system and/or steam system and generating signals ($T_1, T_2 \ldots T_n$) indicative of the sensed temperatures and the times at which they were taken; then correlating time-temperatures readings for $T_1, T_2 \ldots T_n$ to generate a signal representative of the amount of air in the chamber;

comparing this signal to a reference value generated by the Small-Load Compensator Program that will predict the amount of air expected in the sterilizers chamber based on certain independent vales such as chamber size, type of sterilizer, sterilizer manufacturer, number of packs, type of packs and then generating a message responsive to the comparison.

The above description is for the purpose of teaching the person of ordinary skill in the art how to practice the invention, and is not intended to detail all of those obvious modifications and variations of it which will become apparent to the skilled worker upon reading the description. It is intended, however, that all such obvious modifications and variations be included within the scope of the invention which is defined by the following claims. The claims are meant to cover the claimed elements and steps in any arrangement or sequence which is effective to meet the objectives there intended, unless the context specifically indicates the contrary.

I claim:

1. An apparatus for determining the effectiveness of air removal from a steam sterilizer, for the detection of air leaks and for monitoring the sterilization conditions therein, by dynamically channeling air to sensors and monitoring the time-temperature history at the sensors, comprising:
a test module including wall members defining a plurality (n) of test cavities, each having an opening at one end to permit entrance of ambient gases, temperature sensors capable of generating signals ($T_1, T_2, \ldots T_n$) indicative of temperatures at their locations at the ends of the test cavities opposite from said openings, and heat sinks located in said test cavities between said openings and the ends of said test cavities, said heat sinks being capable of condensing steam to thereby concentrate any air present in the direct vicinity of the sensor, said heat sink comprising a material of a density, porosity and thermal conductivity effective to condense a sufficient amount of steam to cause air, if present, to collect at the end of the test device where the temperature sensor is located.

2. An apparatus according to claim 1 which further comprises a data acquisition and transmission unit which includes means for recording the signals $T_1, T_2, \ldots T_n$ and signals representative of the time at which they were taken.

3. An apparatus according to claim 1 wherein said test module includes at least two test cavities containing heat sink materials of different porosities, one to provide an appropriate challenge to the vacuum system to make sure that residual air is not remaining in the heat sink and the other to effective to enable air resulting from leaks within the chamber, vacuum system or steam system to re-enter the heat sink.

4. An apparatus according to claim 1 which further includes:
a data and acquisition and transmission unit which has the capability of recording signals representative of temperatures sensed at defined locations within a sterilization chamber and recording the signals and the signals representative of the time at which they were taken, comprising means for converting analog temperature signals $T_1, T_2, \ldots T_n$ to digital form
means for assigning a time for each temperature signal; and
means for transmitting the signals to a remote location.

5. An apparatus according to claim 1 which further includes a controller comprising:
means for receiving signals ($T_1, T_2, \ldots T_n$) indicative of the temperatures at a number (n) of predetermined locations within the chamber of a steam sterilizer;
means for generating a signal ($T_r$) indicative of a reference temperature;
means for comparing signals $T_1, T_2, \ldots T_n$ to signal $T_r$; and
means for generating a signal indicative of either a pass or fail condition based on the results of the comparison.

6. An apparatus according to claim 5, wherein the means for receiving the signals $T_1, T_2, \ldots T_n$ comprises:
a receiver for radio, infrared or ultrasonic transmission.

7. An apparatus according to claim 5, wherein the means for receiving the signals $T_1, T_2, \ldots T_n$ comprises:
a connector means to electrically couple the controller to the test device.

8. An apparatus for determining the effectiveness of air removal from a steam sterilizer, for the detection of air leaks and for monitoring the sterilization conditions therein, by dynamically channeling air to sensors, monitoring the time-temperature history at the sensors, comprising:
a test device including a test module including at least two test cavities containing heat sink materials of different porosities, one to provide an appropriate challenge to the vacuum system to make sure that residual air is not remaining in the heat sink and the other to effective to enable air resulting from leaks within the chamber, vacuum system or steam system to re-enter the heat sink means, said test modules including means for sensing temperatures at a plurality (n) of locations and generating signals ($T_1, T_2, \ldots T_n$) indicative thereof, and means for generating signals ($T_1, T_2, \ldots T_n$) indicative of a said temperatures at said plurality of locations and the times at which the temperature signals were generated; and
a controller including means for generating a signal ($T_r$) indicative of reference temperature, means for comparing signals $T_1, T_2 \ldots T_n$ to signal $T_r$, and means for generating a signal indicative of either a pass or fail condition based on the results of the comparison.

9. An apparatus according to claim 8 which further comprises a data acquisition and transmission unit which includes a means for recording the signals $T_1, T_2 \ldots T_n$ and signals representative of the time at which they were taken.

10. An apparatus according to claim 9 wherein said data acquisition and transmission unit further includes means for storing the signals $T_1, T_2, \ldots T_n$ for transmission.

11. An apparatus according to claim 8 which further includes:
a data and acquisition and transmission unit which has the capability of recording signals representative of temperatures sensed at defined locations within a sterilization chamber and recording the signals and the signals representative of the time at which they were taken, comprising means for converting analog temperature signals $T_1, T_2, \ldots T_n$ to digital form;
means for assigning a time for each temperature signal; and
means for transmitting the signals to a remote location.

12. An apparatus according to claim 11 wherein the means for receiving the signals $T_1, T_2, \ldots T_n$ comprises:
a receiver for radio, infrared or ultrasonic transmission.

13. A method for determining the effectiveness of air removal from the chamber of a steam sterilizer, for the detection of air leaks by dynamically channeling air to sensors and monitoring the time-temperature history at the sensors, and for monitoring the sterilization conditions within the chamber, comprising:
placing a test device capable of sensing temperatures at a plurality (n) of locations within the chamber of a sterilizer and generating signals ($T_1, T_2, \ldots T_n$) indicative of the sensed temperature, wherein said test device comprises a test module including wall members defining a plurality (n) of test cavities, each having an opening at one end to permit entrance of ambient gases, temperature sensors capable of generating signals ($T_1, T_2, \ldots T_n$) indicative of temperatures at their locations at the ends of the test cavities opposite from said openings, and heat sinks located in said test cavities between said openings and the ends of said test cavities, said heat sinks being capable of condensing steam to thereby concentrate any air present in the direct vicinity of the sensor, said heat sink comprising a material of a density, porosity and thermal conductivity effective to condense a sufficient amount of steam to cause air, if present, to collect at the end of the test device where the temperature sensor is located;

generating signals $T_1, T_2, \ldots T_n$;

generating a signal $T_r$ indicative of a reference temperature;

comparing signals $T_1, T_2 \ldots T_n$ to signal $T_r$, and;

generating a signal indicative of either a pass or fail condition based on the results of the comparison.

14. A method according to claim 13 wherein the method is performed on an empty chamber to provide a test equivalent to a Bowie and Dick test.

15. A method according to claim 13 for determining if a steam sterilizer has been loaded correctly, which further comprises:

providing a controller utilizing a database of information concerning at least one sterilizer and including means for recording the times at which the various temperature readings are taken;

setting the controller to select preprogrammed information regarding the sterilizer used, the type of sterilizer cycle to be run, the type of load and the number of packs in the load to thereby permit testing for proper loading of the sterilizer;

calculating a determination of proper or improper loading based on the comparison of signals $T_1, T_2 \ldots T_n$ to signal $T_r$, the related time information, and the preprogrammed information; and generating a signal indicative of either a pass or fail condition based on the results of the comparison.

16. A method according to claim 13 wherein said test device is further capable of sensing pressure within the chamber and generating a signal $P_c$ indicative of the sensed pressure, and condensed moisture within the test device and generating a signal $M_c$ indicative of the sensed moisture for the purpose of determining sterilizer faults including wet pack conditions and superheat conditions, and the method further comprises:

generating signals $P_c$ and $M_c$;

generating reference signals indicative of a reference pressure $P_r$ and a reference moisture level $M_r$;

comparing signals $P_c$ to $P_r$ and $M_c$ to $M_r$; and generating a signal indicative of either a pass or fail condition based on the results of the comparisons which, in the case of a fail condition, identifies the cause of the failure.

17. A method according to claim 16 for determining if a steam sterilizer is operating correctly and identifying corrective action, wherein said test device is capable of several modes of operation, including a load mode for determining whether a sterilizer is operating correctly, and capable of sensing condensed moisture within the test device and generating a signal $M_c$ indicative of the sensed moisture, and the times at which the various sensed values are taken; said method further comprising:

providing a controller including a database of information concerning the sterilizer, types of cycles of operation, types of loads, and sizes of loads, moisture levels and drying time to reduce moistures from predefined levels to acceptable levels, said controller including means for selecting data relevant to the load being tested;

selecting the load mode of operation on the controller;

generating signal $M_c$;

identifying on the controller the sterilizer that will be used, the type of sterilizer cycle to be run, the type of load and the number of packs to be loaded in the sterilizer;

generating reference signals indicative of a reference moisture level $M_r$;

comparing signal $M_c$ to $M_r$; and generating a signal indicative of either a pass or fail condition based on the results of the comparison, and in the case of a failed condition, generating a signal indicating whether the condition can be corrected and, if so, the additional drying time required.

18. A method according to claim 13 which includes the further step of transmitting the temperature and time signals to a controller outside of the chamber.

19. A method according to claim 13 wherein the test module includes at least two test cavities containing heat sink materials of different porosities such that different degrees of challenge to the entering steam are provided for each.

* * * * *